United States Patent [19]

Rockwell et al.

[11] Patent Number: 5,861,499
[45] Date of Patent: Jan. 19, 1999

[54] NUCLEIC ACID MOLECULES ENCODING THE VARIABLE OR HYPERVARIABLE REGION OF A MONOCLONAL ANTIBODY THAT BINDS TO AN EXTRACELLULAR DOMAIN

[75] Inventors: Patricia Rockwell, West Redding, Conn.; Neil I. Goldstein, Maplewood, N.J.

[73] Assignee: ImClone Systems Incorporated, New York, N.Y.

[21] Appl. No.: 706,804

[22] Filed: Sep. 3, 1996

Related U.S. Application Data

[63] Continuation-in-part of Ser. No. 476,533, Jun. 7, 1995, abandoned, which is a continuation of Ser. No. 326,552, Oct. 20, 1994, which is a continuation-in-part of Ser. No. 196,041, Feb. 10, 1994, abandoned.

[51] Int. Cl.$^6$ ............................ C12N 15/13; C12N 15/16; C12N 15/18; C07K 16/22
[52] U.S. Cl. .................................. 536/23.53; 530/388.1; 530/388.24; 530/389.2
[58] Field of Search ...................... 536/23.53; 530/388.1, 530/388.24, 389.2

[56] References Cited

U.S. PATENT DOCUMENTS 5,270,458  12/1993  Lemischka .

FOREIGN PATENT DOCUMENTS

| 2085291 | 1/1994 | Canada . |
|---|---|---|
| WO 91/02058 | 2/1991 | WIPO . |
| WO 92/14748 | 9/1992 | WIPO . |
| WO 93/11238 | 6/1993 | WIPO . |
| WO 93/12220 | 6/1993 | WIPO . |
| WO 93/21319 | 10/1993 | WIPO . |
| WO 94/10202 | 5/1994 | WIPO . |
| WO 94/10331 | 5/1994 | WIPO . |
| WO 94/11499 | 5/1994 | WIPO . |

OTHER PUBLICATIONS

Folkman, J. and M. Klagsbrun, Science 235, 442–447 (Jan. 23, 1987).
Kapainen et al., J. Exp. Med. 178, 2077–2088 (Dec. 1993).
Kim et al., Nature 362, 841–844 (Apr. 29, 1993).
Matthews et al., PNAS USA 88, 9026–9030 (Oct. 1991).
Millaur et al., Cell 72, 835–846 (1993).
Plate et al., Cancer Research 53, 5822–5827 (Dec. 1, 1993).
Shibuya et al., Oncogene 5, 519–524 (1990).
Terman et al., Oncogene 6, 1677–1683 (1991).
Plate, et al., Nature 359, 845–848 (Oct. 1982).
Leung et al., Science 246, 1306–1309.
Rockwell et al., Molecular and Cellular Differentiation 3, 91–109 (1995).
Rockwell et al., Molecular and Cellular Differentiation 3, 315–335 (1995).

*Primary Examiner*—Susan A. Loring
*Attorney, Agent, or Firm*—Hoffmann & Baron, LLP

[57] ABSTRACT

Nucleic acid molecules comprising a nucleic acid sequence that encodes an amino acid sequence wherein the amino acid sequence consists of the variable region or of the hypervariable region of a monoclonal antibody that specifically binds to an extracellular domain of a VEGF receptor and neutralizes activation of the receptor.

8 Claims, 20 Drawing Sheets

Western Blot of Flk-1/SEAPS Immunoprecipitation with MAb DC101

Inhibition of VEGF-Flk-1/fms activation by pre-bound MAb DC101

Assay conditions:
MAb (5µg/ml):  −  +  −  −  P/+  C/+
VEGF (ng/ml):  −  −  20  40  40  40

− 200

Probe: Anti-Ptyr

Assay conditions: P: MAb pre-bound 15'; VEGF 15'
C: Competitive assay; MAb + VEGF 15'

FIGURE 6 FACS ANALYSIS OF Anti-flk-1 MAb BINDING TO flk-1/fms TRANSFECTED 3T3 CELLS (C441)

FIGURE 7 SATURATION BINDING OF MAb DC101 TO THE flk-1/fms RECEPTOR ON THE TRANSFECTED 3T3 CELL LINE C441

Immunoprecipitation of phosphorylated Flk-1/fms from VEGF stimulated Flk-1/fms transfected 3T3 cells Antibodies: 1) Rat anti-flk-2 IgG$_{2a}$ 2A13
2) Rat anti-flk-1 IgG$_1$ DC101
3) Rat anti-flk-2 IgG$_1$ 23H7
4) Rabbit anti-fms polyclonal IM 133

Sensitivity of VEGF induced phosphorylation of the Flk-1/fms receptor to inhibition by MAb DC101

Effect of MAb DC101 on CSF-1 induced phosphorylation of the fms receptor

| MAb (5µg/ml) | - | + | - | - | + | + |
| CSF-1 (ng/ml) | - | - | 20 | 40 | 20 | 40 |

Probe: Anti-Ptyr

Specificity of MAb DC101 neutralization of the activated Flk-1/fms receptor

Immunoprecipitation of phosphorylated receptor bands from VEGF stimulated HUVEC cells

FIGURE 16A TREAMENT OF GLIOBLASTOMA XENOGRAFTS WITH RAT anti-flk-1 MAb
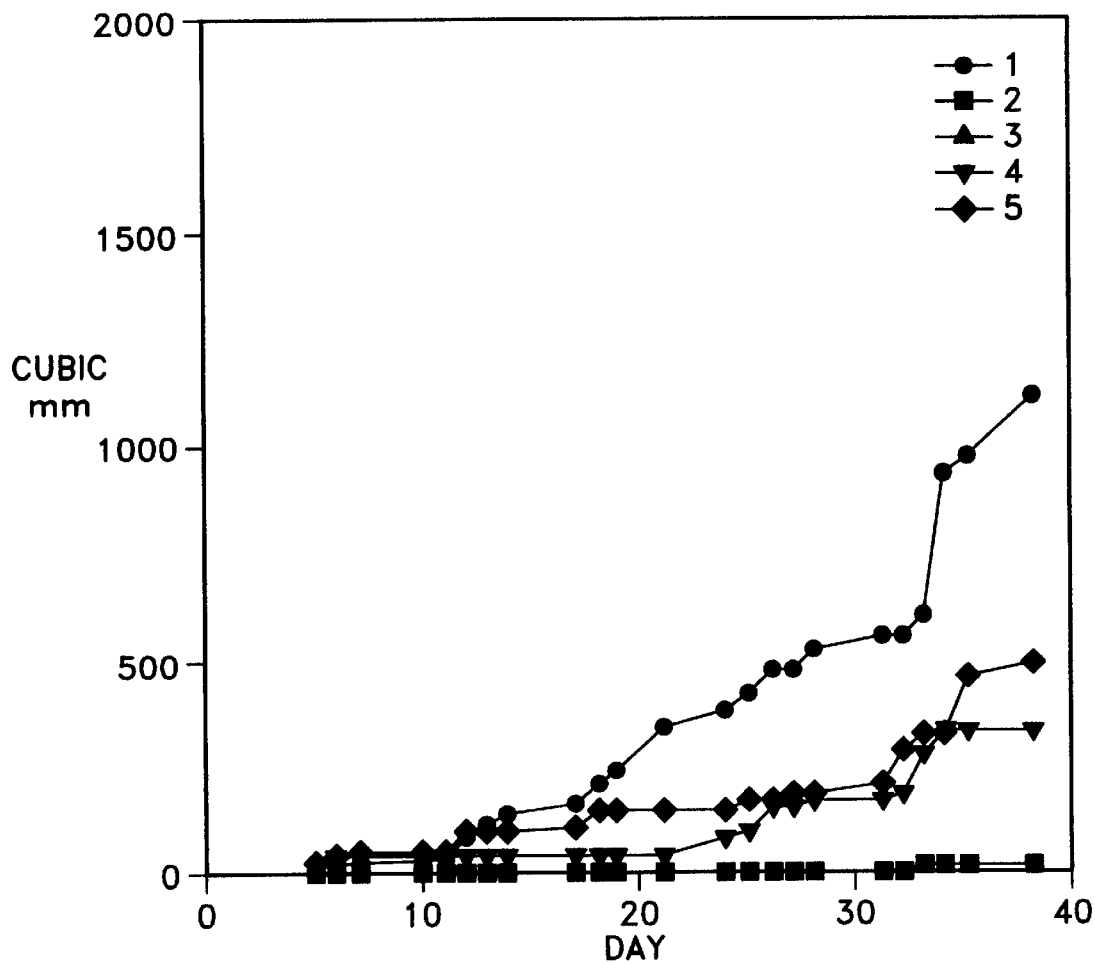
STATISICAL ANALYSIS
flk-1 SLOPE = 16.09
p VALUE FOR flk-1 VERSUS flk-2 TUMOR SIZE = 0.0001

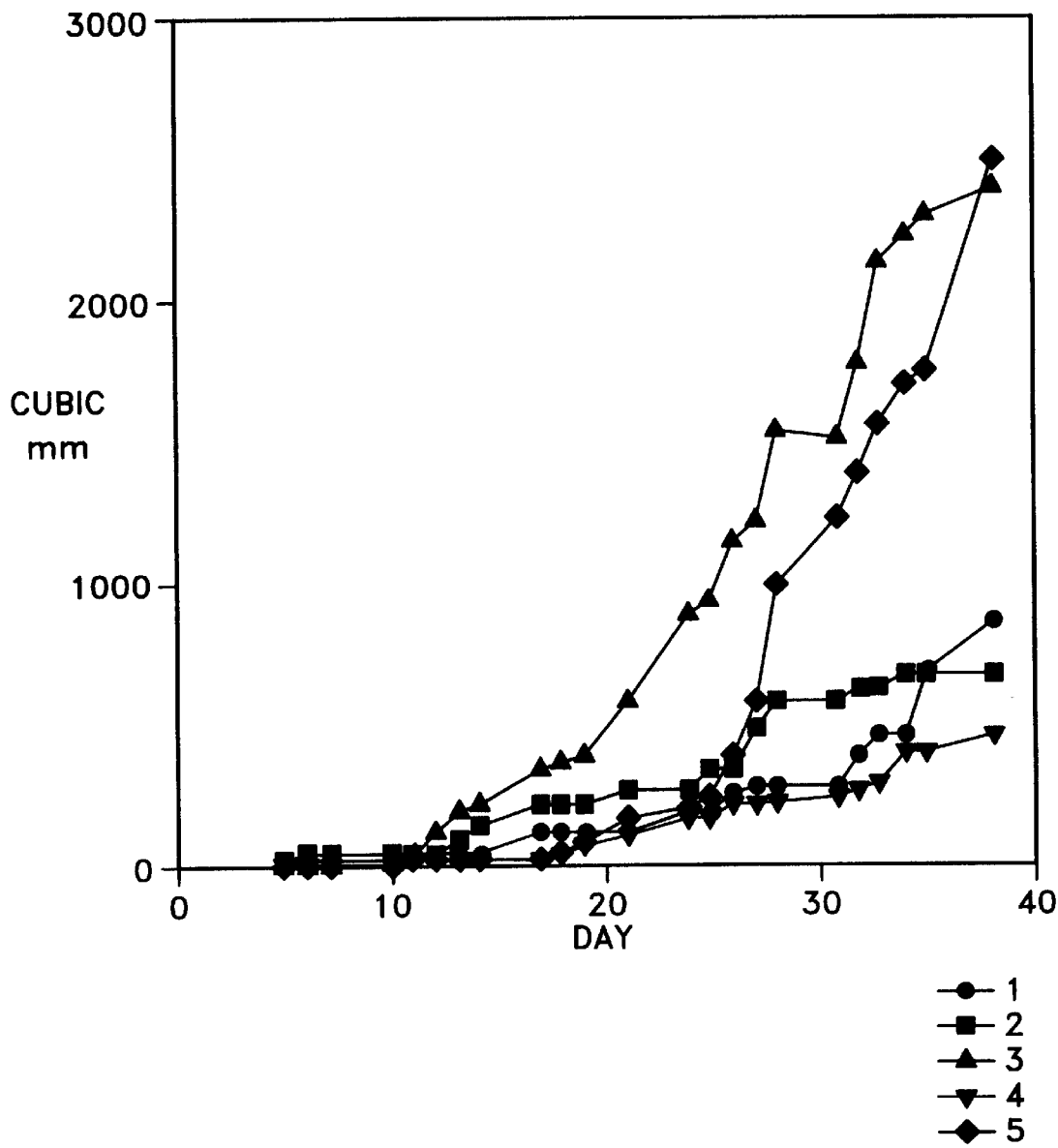
FIGURE 16B TREAMENT OF GLIOBLASTOMA XENOGRAFTS WITH RAT anti-flk-2 MAb
STATISICAL ANALYSIS
flk-2 SLOPE = 37.39
p VALUE FOR flk-1 VERSUS flk-2 TUMOR SIZE = 0.0001

NUCLEIC ACID MOLECULES ENCODING THE VARIABLE OR HYPERVARIABLE REGION OF A MONOCLONAL ANTIBODY THAT BINDS TO AN EXTRACELLULAR DOMAIN

This application is a continuatiion-in-part of Ser. No. 08/476,533 filed Jun. 27, 1995, now abandoned; which is a continuation of Ser. No. 08/326,552 filed Oct. 20, 1994, pending; which is a continuation-in-part of Ser. No. 08/196,041, filed Feb. 10, 1994, abandoned.

BACKGROUND OF THE INVENTION

Angiogenesis is the process of developing new blood vessels that involves the proliferation, migration and tissue infiltration of capillary endothelial cells from pre-existing blood vessels. Angiogenesis is important in normal physiological processes including embryonic development, follicular growth, and wound healing as well as in pathological conditions involving tumor growth and non-neoplastic diseases involving abnormal neovascularization, including neovascular glaucoma (Folkman, J. and Klagsbrun, M. Science 235:442–447 (1987)).

The vascular endothelium is usually quiescent and its activation is tightly regulated during angiogenesis. Several factors have been implicated as possible regulators of angiogenesis in vivo. These include transforming growth factor (TGFb), acidic and basic fibroblast growth factor (aFGF and bFGF), platelet derived growth factor (PDGF), and vascular endothelial growth factor (VEGF) (Klagsbrun, M. and D'Amore, P. (1991) Annual Rev. Physiol. 53: 217–239). VEGF, an endothelial cell-specific mitogen, is distinct among these factors in that it acts as an angiogenesis inducer by specifically promoting the proliferation of endothelial cells.

VEGF is a homodimeric glycoprotein consisting of two 23 kD sub units with structural similarity to PDGF. Four different monomeric isoforms of VEGF exist resulting from alternative splicing of mRNA. These include two membrane bound forms ($VEGF_{206}$ and $VEGF_{189}$) and two soluble forms ($VEGF_{165}$ and $VEGF_{121}$). In all human tissues except placenta, $VEGF_{165}$ is the most abundant isoform.

VEGF is expressed in embryonic tissues (Breier et al., Development (Camb.) 114:521 (1992)), macrophages, proliferating epidermal keratinocytes during wound healing (Brown et al., J. Exp. Med., 176:1375 (1992)), and may be responsible for tissue edema associated with inflammation (Ferrara et al., Endocr. Rev. 13:18 (1992)). In situ hybridization studies have demonstrated high VEGF expression in a number of human tumor lines including glioblastoma multiform, hemangioblastoma, central nervous system neoplasms and AIDS-associated Kaposi's sarcoma (Plate, K. et al. (1992) Nature 359: 845–848; Plate, K. et al. (1993) Cancer Res. 53: 5822–5827; Berkman, R. et al. (1993) J. Clin. Invest. 91: 153–159; Nakamura, S. et al. (1992) AIDS Weekly, 13 (1)). High levels of VEGF were also observed in hypoxia induced angiogenesis (Shweiki, D. et al. (1992) Nature 359: 843–845).

The biological response of VEGF is mediated through its high affinity VEGF receptors which are selectively expressed on endothelial cells during embryogenesis (Millauer, B., et al. (1993) Cell 72: 835–846) and during tumor formation. VEGF receptors typically are class IIII receptor-type tyrosine kinases characterized by having several, typically 5 or 7, immunoglobulin-like loops in their amino-terminal extracellular receptor ligand-binding domains (Kaipainen et al., J. Exp. Med. 178:2077–2088 (1993)). The other two regions include a transmembrane region and a carboxy-terminal intracellular catalytic domain interrupted by an insertion of hydrophilic interkinase sequences of variable lengths, called the kinase insert domain (Terman et al., Oncogene 6:1677–1683 (1991). VEGF receptors include FLT-1, sequenced by Shibuya M. et al., Oncogene 5, 519–524 (1990); KDR, described in PCT/US92/01300, filed Feb.20, 1992, and in Terman et al., Oncogene 6:1677–1683 (1991); and FLK-1, sequenced by Matthews W. et al. Proc. Natl. Acad. Sci. USA, 88:9026–9030 (1991).

High levels of FLK-1 are expressed by endothelial cells that infiltrate gliomas (Plate, K. et al., (1992) Nature 359: 845–848). FLK-1 levels are specifically upregulated by VEGF produced by human glioblastomas (Plate, K. et al. (1993) Cancer Res. 53: 5822–5827). The finding of high levels of FLK-1 expression in glioblastoma associated endothelial cells (GAEC) indicates that receptor activity is probably induced during tumor formation since FLK-1 transcripts are barely detectable in normal brain endothelial cells. This upregulation is confined to the vascular endothelial cells in close proximity to the tumor. Blocking VEGF activity with neutralizing anti-VEGF monoclonal antibodies (mAbs) resulted in an inhibition of the growth of human tumor xenografts in nude mice (Kim, K. et al. (1993) Nature 362: 841–844), indicating a direct role for VEGF in tumor-related angiogenesis.

Although the VEGF ligand is upregulated in tumor cells, and its receptors are upregulated in tumor infiltrated vascular endothelial cells, the expression of the VEGF ligand and its receptors is low in normal cells that are not associated with angiogenesis. Therefore, such normal cells would not be affected by blocking the interaction between VEGF and its receptors to inhibit angiogenesis, and therefore tumor growth. Blocking this VEGF-VEGF receptor interaction by using a monoclonal antibody to the VEGF receptor has not been demonstrated prior to the subject invention.

One advantage of blocking the VEGF receptor as opposed to blocking the VEGF ligand to inhibit angiogenesis, and thereby to inhibit pathological conditions such as tumor growth, is that fewer antibodies may be needed to achieve such inhibition. Furthermore, receptor expression levels may be more constant than those of the environmentally induced ligand. Another advantage of blocking the VEGF receptor is that more efficient inhibition may be achieved when combined with blocking of the VEGF ligand.

The object of this invention is to provide monoclonal antibodies that neutralizes the interaction between VEGF and its receptor by binding to a VEGF receptor and thereby preventing VEGF phosphorylation of the receptor. A further object of this invention is to provide methods to inhibit angiogenesis and thereby to inhibit tumor growth in mammals using such monoclonal antibodies.

SUMMARY OF THE INVENTION

The present invention provides a monoclonal antibody which specifically binds to an extracellular domain of a VEGF receptor and neutralizes activation of the receptor.

The invention also provides hybridoma cell lines as well as the monoclonal antibodies produced therefrom: DC101 (lgG1k) deposited as ATCC Accession No. ATCC HB 11534: Mab25 (lgG1) deposited as HB12152; and Mab 73 (lgG1) deposited as HB-12153.

Further, the invention provides a method of neutralizing VEGF activation of a VEGF receptor in endothelial cells comprising contacting the cells with the monoclonal antibody of the invention.

The invention also provides a method of inhibiting angiogenesis in a mammal comprising administering an effective amount of any one of the antibodies of the invention to the mammal. In addition, the invention provides a method of inhibiting tumor growth in a mammal comprising administering an effective amount of any one of the antibodies of the invention to the mammal. The invention also provides a pharmaceutical composition comprising any one of the antibodies of the invention and a pharmaceutically acceptable carrier.

DESCRIPTION OF THE FIGURES

FIG. 2A: Competitive inhibition assay indicating the effect of anti-FLK-1 monoclonal antibody DC101 on $VEGF_{165}$ induced phosphorylation of the FLK-1/fms receptor in transfected 3T3 cells. FIG. 2B: Sensitivity of VEGF induced phosphorylation of the FLK-1/fms receptor to inhibition by monoclonal antibody DC101. C441 cells were assayed at stimulatory concentrtions of $VEGF_{165}$ (40 ng/ml) combined with varying levels of the antibody.

FIG. 3A: Titration of VEGF-induced phosphorylation of the FLK-1/fms receptor in the presence of mAb DC101. CC441 cells were stimulated with the concentrations of VEGF indicated in the presence (Lanes 1 to 4) or absence (Lanes 5 to 8) of 5 ug/ml of Mab DC101. Unstimulated cells assayed in the presence of antibody (Lane 9) serves as the control. FIG. 3B: Densitometry scans of the level of phosphorylated receptor in each lane in FIG. 3A relative to each VEGF concentration are plotted to show the extent of Mab inhibition at excess ligand concentrations. Cell lystes were prepared for detection by anti-phosphotyrosine as discribed in the Examples below.

FIGS. 16A and 16B: FIG. 16A: Reduction in tumor growth of individual animals with DC101 (rat anti-flk-1 monoclonal antibody). FIG. 16B: Reduction in tumor growth in individual animals with the control 2A13 group (rat anti-flk-2 monoclonal antibody).

DETAILED DESCRIPTION OF THE INVENTION

Figure 1:
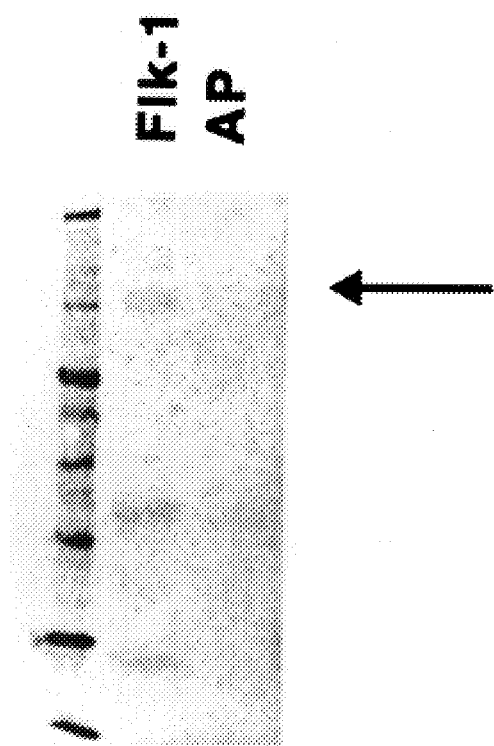
FIG. 1: Western Blot of FLK-1/SEAPS immunoprecipitation with monoclonal antibody DC1O1 demonstrating that DC101 immunoprecipitates murine FLK-1 :SEAPS but not SEAPS alone.

The present invention provides monoclonal antibodies that bind specifically to an extracellular domain of a VEGF receptor. An extracellular domain of a VEGF receptor is herein defined as a ligand-binding domain on extracellular region of the receptor, normally found at the amino-terminal end of the protein, typical of class III tyrosine kinase receptors.

Some examples of VEGF receptors include the protein tyrosine kinase receptors referred to in the literature as FLT-1, KDR and FLK-1. Unless otherwise stated or clearly inferred otherwise by context, this specification will follow the customary literature nomenclature of VEGF receptors. KDR will be referred to as the human form of a VEGF receptor having MW 180 kD. FLK-1 will be referred to as the murine homolog of KDR. FLT-1 will be referred to as a form of VEGF receptor different from, but related to, the KDR/FLK-1 receptor.

Other VEGF receptors include those that can be cross-link labeled with VEGF, or that can be co-immunoprecipitated with KDR (MW 180 KD). Some known forms of these VEGF receptors have molecular weights of approximately 170 KD, 150 KD, 130–135 KD, 120–125 KD and 85 KD. See, for example, Quinn et al. Proc. Nat'l. Acad. Sci 90, 7533–7537 (1993). Scher et al. J. Biol. Chem. 271, 5761–5767 (1996).

Equivalent receptors having substantially the same amino acid sequence, as defined above, occur in mammals, ie human, mouse. The binding of an antibody to one VEGF receptor does not necessarily imply binding to another VEGF receptor, and binding to a VEGF receptor in one mammal does not necessarily imply binding to the equivalent receptor in another mammal.

The VEGF receptor is usually bound to a cell, such as an endothelial cell. The VEGF receptor may also be bound to a non-endothelial cell, such as a tumor cell. Alternatively, the VEGF receptor may be free from the cell, preferably in soluble form.

The antibodies of the invention neutralize VEGF receptors. In this specification, neutralizing a receptor means inactivating the intrinsic kinase activity of the receptor to transduce a signal. A reliable assay for VEGF receptor neutralization is the inhibition of receptor phosphorylation.

The present invention is not limited by any particular mechanism of VEGF receptor neutralization. At the time of filing this application, the mechanism of VEGF receptor neutralization by antibodies is not well understood, and the mechanism followed by one antibody is not necessarilly the same as that followed by another antibody. Some possible mechanisms include preventing binding of the VEGF ligand to the extracellular binding domain of the VEGF receptor, and preventing dimerization or oligomerization of receptors. Other mechanisms cannot, however, be ruled out.

UTILITY

A. Neutralizing VEGF activation of VEGF receptors:

Neutralization of VEGF activation of a VEGF receptor in a sample of endothelial or non-endothelial cells, such as tumor cells, may be performed in vitro orin vivo. Neutralizing VEGF activation of a VEGF receptor in a sample of VEGF-receptor expressing cells comprises contacting the cells with an antibody of the invention. In vitro, the cells are contacted with the antibody before, simultaneously with, or after, adding VEGF to the cell sample.

In vivo, an antibody of the invention is contacted with a VEGF receptor by administration to a mammal. Methods of administration to a mammal include, for example, oral, intravenous, intraperitoneal, subcutaneous, or intramuscular administration.

This in vivo neutralization method is useful for inhibiting angiogenesis in a mammal. Angiogenesis inhibition is a useful therapeutic method, such as for preventing or inhibiting angiogenesis associated with pathological conditions such as tumor growth. Accordingly, the antibodies of the invention are anti-angiogenic and antitumor immunotherapeutic agents.

VEGF receptors are found on some non-endothelial cells, such as tumor cells, indicating the unexpected presence of an autocrine and/or paracrine loop in these cells. The antibodies of this invention are useful in neutralizing activity of VEGF receptors on such cells, thereby blocking the autocrine and/or paracrine loop, and inhibiting tumor growth.

The methods of inhibiting angiogenesis and of inhibiting pathological conditions such as tumor growth in a mammal comprises administering an effective amount of any one of the invention's antibodies systemically to a mammal, or directly to a tumor within the mammal. The mammal is preferably human. This method is effective for treating subjects with carcinomas or sarcomas, especially highly vascular tumors such as Kaposi's sarcoma, CNS neoplasms (capillary hemangioblastomas, meningiomas and cerebral metastases), melanoma, gastrointestinal and renal sarcomas, rhabdomyosarcoma, glioblastoma, preferably glioblastoma multiform, and leiomyosarcoma.

Experimental results described later demonstrate that antibodies of the invention specifically block VEGF induced phosphorylation of a mouse extracellular FLK-1/intracellular fms chimeric receptor expressed in transfected 3T3 cells. The antibodies had no effect on a fully stimulated chimeric extracellular fms/intracellular FLK2 receptor by CSF-1. In vivo studies also described below show that the antibodies were able to significantly inhibit tumor growth in nude mice.

A cocktail of monoclonal antibodies of the invention provides an especially efficient treatment for inhibiting the growth of tumor cells. The cocktail may include as few as 2, 3 or 4 antibodies, and as many as 6, 8 or 10 antibodies.

The combined treatment of one or more of the antibodies of the invention with anti-VEGF antibodies provides a more efficient treatment for inhibiting the growth of tumor cells than the use of the antibody or antibodies alone. Anti-VEGF antibodies have been described by Kim et al in Nature 362, 841–844 (1993).

Furthermore, the combined treatment of one or more of the antibodies of the invention with an anti-neoplastic or chemotherapeutic drug such as, for example, doxorubicin, cisplatin or taxol provides an even more efficient treatment for inhibiting the growth of tumor cells than the use of the antibody by itself. In one embodiment, the pharmaceutical composition comprises the antibody and the anti-neoplastic or chemotherapeutic drug as separate molecules. In another embodiment, the pharmaceutical composition comprises the antibody attached, such as, for example, by conjugation, to an chemotherapeutic drug.

Preventing or inhibiting angiogenesis is also useful to treat non-neoplastic pathologic conditions charaqcterized by excessive angiogenesis, such as neovascular glaucoma, proliferative retinopathy including proliferative diabetic retinopathy, macular degeneration, hemangiomas, angiofibromas, and psoriasis.

B. Using the Antibodies of the Invention to Isolate and Purify the VEGF Receptor The antibodies of the present invention may be used to isolate and purify the VEGF receptor using conventional methods such as affinity chromatography (Dean, P. D. G. et al., Affinity Chromatography: A Practical Approach, IRL Press, Arlington, Va. (1985)). Other methods well known in the art include magnetic separation with antibody-coated magnetic beads, "panning" with an antibody attached to a solid matrix, and flow cytometry.

The source of VEGF receptor is typically vascular cells, and especially vascular endothelial cells, that express the VEGF receptor. Suitable sources of vascular endothelial cells are blood vessels, such as umbilical cord blood cells, especially, human umbilical cord vascular endothelial cells (HUVEC).

The VEGF receptors may be used as starting material to produce other materials, such as antigens for making additional monoclonal and polyclonal antibodies that recognize and bind to the VEGF receptor or other antigens on the surface of VEGFexpressing cells.

C. Using the Antibodies of the Invention to Isolate and Purify FLK-1 Positive Tumor Cells The antibodies of the present invention may be used to isolate and purify FLK-1 positive tumor cells, i.e., tumor cells expressing the FLK-1 receptor, using conventional methods such as affinity chromatography (Dean, P. D. G. et al., Affinity Chromatography:A Practical Approach, IRL Press, Arlington, Va. (1985)). Other methods well known in the art include magnetic separation with antibody-coated magnetic beads, cytotoxic agents, such as complement, conjugated to the antibody, "panning" with an antibody attached to a solid matrix, and flow cytometry.

D. Monitoring Levels of VEGF and VEGF Receptors In Vitro or In Vivo

The antibodies of the invention may be used to monitor levels of VEGF or VEGF receptors in vitro or in vivo in biological samples using standard assays and methods known in the art. Some examples of biological samples include bodily fluids, such as blood. Standard assays involve, for example, labeling the antibodies and conducting standard immunoassays, such as radioimmunoassays, as is well know in the art.

PREPARATION OF ANTIBODIES

The monoclonal antibodies of the invention that specifically bind to the VEGF receptor may be produced by methods known in the art. These methods include the immunological method described by Kohler and Milstein in Nature 256, 495–497 (1975) and Campbell in "Monoclonal Antibody Technology, The Production and Characterization of Rodent and Human Hybridomas" in Burdon et al., Eds., Laboratory Techniques in Biochemistry and Molecular Biology, Volume 13, Elsevier Science Publishers, Amsterdam (1985); as well as by the recombinant DNA method described by Huse et al in Science 246, 1275–1281 (1989).

The antibodies of the invention may be prepared by immunizing a mammal with a soluble VEGF receptor. The soluble receptors may be used by themselves as immunogens, or may be attached to a carrier protein or to other objects, such as beads, i.e. sepharose beads. After the mammal has produced antibodies, a mixture of antibody-producing cells, such as the splenocytes, is isolated. Monoclonal antibodies may be produced by isolating individual antibody-producing cells from the mixture and making the cells immortal by, for example, fusing them with tumor cells, such as myeloma cells. The resulting hybridomas are preserved in culture, and express monoclonal antibodies, which are harvested from the culture medium.

The antibodies may also be prepared from VEGF receptors bound to the surface of cells that express the VEGF receptor. The cell to which the VEGF receptors are bound may be a cell that naturally expresses the receptor, such as a vascular endothelial cell. Alternatively, the cell to which the receptor is bound may be a cell into which the DNA encoding the receptor has been transfected, such as 3T3 cells.

The antibody may be prepared in any mammal, including mice, rats, rabbits, goats and humans. The antibody may be a member of one of the following immunoglobulin classes: IgG, IgM, IgA, IgD, or IgE, and the subclasses thereof, and preferably is an IgG1 antibody.

In one embodiment the antibody is a monoclonal antibody directed to an epitope of a VEGF receptor present on the surface of a cell. In another embodiment the monoclonal antibody is a rat IgG1 monoclonal antibody, specific for the murine VEGF receptor FLK-1, and produced by hybridoma DC101. Hybridoma cell line DC101 was deposited Jan. 26, 1994 with the American Type Culture Collection, designated ATCC HB 11534. In a preferred embodiment, the monoclonal antibody is directed to an epitope of a human FLT-1 receptor or to a human KDR receptor.

Functional Equivalents of Antibodies

The invention also includes functional equivalents of the antibodies described in this specification. Functional equivalents have binding characteristics comparable to those of the antibodies, and include, for example, chimerized, humanized and single chain antibodies as well as fragments thereof. Methods of producing such functional equivalents are disclosed in PCT Application WO 93/21319, European Patent Application No. 239,400; PCT Application WO 89/09622; European Patent Application 338,745; and European Patent Application EP 332,424.

Functional equivalents include polypeptides with amino acid sequences substantially the same as the amino acid sequence of the variable or hypervariable regions of the antibodies of the invention. "Substantially the same" amino acid sequence is defined herein as a sequence with at least 70%, preferably at least about 80%, and more preferably at least about 90% homology to another amino acid sequence, as determined by the FASTA search method in accordance with Pearson and Lipman, Proc. Natl. Acad. Sci. USA 85, 2444–2448 (1988).

Chimerized antibodies preferably have constant regions derived substantially or exclusively from human antibody constant regions and variable regions derived substantially or exclusively from the sequence of the variable region from a mammal other than a human. Humanized antibodies preferably have constant regions and variable regions other than the complement determining regions (CDRs) derived substantially or exclusively from the corresponding human antibody regions and CDRs derived substantially or exclusively from a mammal other than a human.

Suitable mammals other than a human include any mammal from which monoclonal antibodies may be made. Suitable examples of mammals other than a human include, for example a rabbit, rat, mouse, horse, goat, or primate. Mice are preferred.

Single chain antibodies or Fv fragments are polypeptides that consist of the variable region of the heavy chain of the antibody linked to the variable region of the light chain with or without an interconnecting linker. Thus, the Fv comprises the entire antibody combining site. These chains may be produced in bacteria.

Functional equivalents further include fragments of antibodies that have the same, or binding characteristics comparable to, those of the whole antibody. Such fragments may contain one or both Fab fragments or the F(ab')$_2$ fragment. Preferably the antibody fragments contain all six complement determining regions of the whole antibody, although fragments containing fewer than all of such regions, such as three, four or five CDRs, are also functional.

Further, the functional equivalents may be or may combine members of any one of the following immunoglobulin classes: IgG, IgM, IgA, IgD, or IgE, and the subclasses thereof.

Preparation of VEGF Receptor Immunogens

The VEGF receptor may be used as an immunogen to raise an antibody of the invention. The receptor peptide may be obtained from natural sources, such as from cells that express VEGF receptors, i.e. vascular endothelial cells. Alternatively, synthetic VEGF receptor peptides may be prepared using commercially available machines and the VEGF receptor amino acid sequence provided by, for example, Shibuya M. et al., Oncogene 5, 519–524 (1990) for FLT-1; PCT/US92/01300 and Terman et al., Oncogene 6:1677–1683 (1991) for KDR; and Matthews W. et al. Proc. Natl. Acad. Sci. USA, 88:9026–9030 (1991) for FLK-1.

As a further alternative, DNA encoding a VEGF receptor, such as a cDNA or a fragment thereof, may be cloned and expressed and the resulting polypeptide recovered and used as an immunogen to raise an antibody of the invention. In order to prepare the VEGF receptors against which the antibodies are made, nucleic acid molecules that encode the VEGF receptors of the invention, or portions thereof, especially the extracellular portions thereof, may be inserted into known vectors for expression in host cells using standard recombinant DNA techniques, such as those described below. Suitable sources of such nucleic acid molecules include cells that express VEGF receptors, i.e. vascular endothelial cells.

Preparation of Equivalents

Equivalents of antibodies are prepared by methods known in the art. For example, fragments of antibodies may be prepared enzymatically from whole antibodies.

Preferably, equivalents of antibodies are prepared from DNA encoding such equivalents. DNA encoding fragments of antibodies may be prepared by deleting all but the desired portion of the DNA that encodes the full length antibody.

DNA encoding chimerized antibodies may be prepared by recombining DNA substantially or exclusively encoding human constant regions and DNA encoding variable regions derived substantially or exclusively from the sequence of the variable region of a mammal other than a human. DNA encoding humanized antibodies may be prepared by recombining DNA encoding constant regions and variable regions other than the complementarity determining regions (CDRs) derived substantially or exclusively from the corresponding human antibody regions and DNA encoding CDRs derived substantially or exclusively from a mammal other than a human.

Suitable sources of DNA molecules that encode fragments of antibodies include cells, such as hybridomas, that express the full length antibody. The fragments may be used by themselves as antibody equivalents, or may be recombined into equivalents, as described above.

The DNA deletions and recombinations described in this section may be carried out by known methods, such as those described in the published patent applications listed above in the section entitled "Functional Equivalents of Antibodies" and/or other standard recombinant DNA techniques, such as those described below.

Standard Recombinant DNA Techniques

Standard recombinant DNA techniques are described in Sambrook et al., "Molecular Cloning," Second Edition, Cold Spring Harbor Laboratory Press (1987) and by Ausubel et al. (Eds) "Current Protocols in Molecular Biology," Green Publishing Associates/Wiley-Interscience, New York (1990).

Briefly, a suitable source of cells containing nucleic acid molecules that express the desired DNA, such as an antibody, antibody equivalent or VEGF receptor, is selected. See above.

Total RNA is prepared by standard procedures from a suitable source. The total RNA is used to direct cDNA synthesis. Standard methods for isolating RNA and synthesizing cDNA are provided in standard manuals of molecular biology such as, for example, those described above.

The cDNA may be amplified by known methods. For example, the cDNA may be used as a template for amplification by polymerase chain reaction (PCR); see Saiki et al., Science, 239, 487 (1988) or Mullis et al., U.S. Pat. No. 4,683,195. The sequences of the oligonucleotide primers for the PCR amplification are derived from the known sequence to be amplified. The oligonucleotides are synthesized by methods known in the art. Suitable methods include those described by Caruthers in Science 230, 281–285 (1985).

A mixture of upstream and downstream oligonucleotides are used in the PCR amplification. The conditions are optimized for each particular primer pair according to standard procedures. The PCR product is analyzed, for example, by electrophoresis for cDNA having the correct size, corresponding to the sequence between the primers.

Alternatively, the coding region may be amplified in two or more overlapping fragments. The overlapping fragments are designed to include a restriction site permitting the assembly of the intact cDNA from the fragments.

In order to isolate the entire protein-coding regions for the VEGF receptors, for example, the upstream PCR oligonucleotide primer is complementary to the sequence at the 5' end, preferably encompassing the ATG start codon and at least 5–10 nucleotides upstream of the start codon. The downstream PCR oligonucleotide primer is complementary to the sequence at the 3' end of the desired DNA sequence. The desired DNA sequence preferably encodes the entire extracellular portion of the VEGF receptor, and optionally encodes all or part of the transmembrane region, and/or all or part of the intracellular region, including the stop codon.

The DNA to be amplified, such as that encoding antibodies, antibody equivalents, or VEGF receptors, may also be replicated in a wide variety of cloning vectors in a wide variety of host cells. The host cell may be prokaryotic or eukaryotic.

The vector into which the DNA is spliced may comprise segments of chromosomal, non-chromosomal and synthetic DNA sequences. Some suitable prokaryotic cloning vectors include plasmids from *E. coli,* such as colE1, pCR1, pBR322, pMB9, pUC, pKSM, and RP4. Prokaryotic vectors also include derivatives of phage DNA such as M13 and other filamentous single-stranded DNA phages.

A preferred vector for cloning nucleic acid encoding the VEGF receptor is the Baculovirus vector.

The vector containing the DNA to be expressed is transfected into a suitable host cell. The host cell is maintained in an appropriate culture medium, and subjected to conditions under which the cells and the vector replicate. The vector may be recovered from the cell. The DNA to be expressed may be recovered from the vector.

Expression and Isolation of Antibodies, Antibody Equivalents, or VEGF Receptors

The DNA to be expressed, such as that encoding antibodies, antibody equivalents, or VEGF receptors, may be inserted into a suitable expression vector and expressed in a suitable prokaryotic or eucaryotic host cell.

For example, the DNA inserted into a host cell may encode the entire extracellular portion of the VEGF receptor, or a soluble fragment of the extracellular portion of the VEGF receptor. The extracellular portion of the VEGF receptor encoded by the DNA is optionally attached at either, or both, the 5' end or the 3' end to additional amino acid sequences. The additional amino acid sequences may be attached to the VEGF receptor extracellular region in nature, such as the leader sequence, the transmembrane region and/or the intracellular region of the VEGF receptor. The additional amino acid sequences may also be sequences not attached to the VEGF receptor in nature. Preferably, such additional amino acid sequences serve a particular purpose, such as to improve expression levels, secretion, solubility, or immunogenicity.

Vectors for expressing proteins in bacteria, especially *E. coli,* are known. Such vectors include the PATH vectors described by Dieckmann and Tzagoloff in J. Biol. Chem. 260, 1513–1520 (1985). These vectors contain DNA sequences that encode anthranilate synthetase (TrpE) followed by a polylinker at the carboxy terminus. Other expression vector systems are based on beta-galactosidase (pEX); lambda PL; maltose binding protein (pMAL); and glutathione S-transferase (PGST) -see Gene 67, 31 (1988) and Peptide Research 3, 167 (1990). Vectors useful in yeast are available. A suitable example is the 2μ plasmid.

Suitable vectors for expression in mammalian cells are also known. Such vectors include well-known derivatives of SV-40, adenovirus, retrovirus-derived DNA sequences and shuttle vectors derived from combination of functional mammalian vectors, such as those described above, and functional plasmids and phage DNA.

Further eukaryotic expression vectors are known in the art (e.g., P. J. Southern and P. Berg, J. Mol. Appl. Genet. 1, 327–341 (1982); S. Subramani et al, Mol. Cell. Biol. 1, 854–864 (1981); R. J. Kaufmann and P. A. Sharp, "Amplification And Expression Of Sequences Cotransfected with A Modular Dihydrofolate Reductase Complementary DNA Gene," J. Mol. Biol. 159, 601–621 (1982); R. J. Kaufmann and P. A. Sharp, Mol. Cell. Biol. 159, 601–664 (1982); S. I. Scahill et al, "Expression And Characterization Of The Product Of A Human Immune Interferon DNA Gene In Chinese Hamster Ovary Cells," Proc. Natl. Acad. Sci. USA 80, 4654–4659 (1983); G. Urlaub and L. A. Chasin, Proc. NatI. Acad. Sci. USA 77, 4216–4220, (1980).

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Vectors containing the control signals and DNA to be expressed, such as that encoding antibodies, antibody equivalents, or VEGF receptors, are inserted into a host cell for expression. Some useful expression host cells include well-known prokaryotic and eukaryotic cells. Some suitable prokaryotic hosts include, for example, *E. coli,* such as *E. coli* SG-936, *E. coli* HB 101, *E. coli* W31 10, *E. coli* X1776, *E. coli* X2282, *E. coli* DHI, and *E. coli* MRCI, Pseudomonas, Bacillus, such as *Bacillus subtilis,* and Streptomyces. Suitable eukaryotic cells include yeast and other fungi, insect, animal cells, such as COS cells and CHO cells, human cells and plant cells in tissue culture.

Following expression in a host cell maintained in a suitable medium, the polypeptide or peptide to be expressed, such as that encoding antibodies, antibody equivalents, or VEGF receptors, may be isolated from the medium, and purified by methods known in the art. If the, the polypeptide or peptide is not secreted into the culture medium, the host cells are lysed prior to isolation and purification.

EXAMPLES

The Examples which follow are set forth to aid in understanding the invention but are not intended to, and should not be construed to, limit its scope in any way. The Examples do not include detailed descriptions of conventional methods, such as those employed in the construction of vectors and plasmids, the insertion of genes encoding polypeptides into such vectors and plasmids, or the introduction of plasmids into host cells. Such methods are well known to those of ordinary skill in the art and are described in numerous publications including Sambrook, J., Fritsch, E. F. and Maniatis, T. (1989) Molecular Cloning: A Laboratory Manual, 2nd edition, Cold Spring Harbor Laboratory Press.

Example I. Cell Lines and Media

NIH 3T3 cells were obtained from the American Type Culture Collection (Rockville Md). The C441 cell line was constructed by transfecting 3T3 cells with the chimeric receptor mouse FLK1/human fms. 10A2 is a 3T3 transfectant containing the chimeric receptor human fms/mouse FLK2, the isolation and characterization of which has been described (Dosil, M. et al., Mol. Cell. Biol. 13:6572–6585 (1993)). Cells were routinely maintained in Dulbecco's modified Eagle's medium (DME) supplemented with 10% calf serum (CS), 1 mM L-glutamine, antibiotics, and 600 ug/ml G418 (Geneticin; Sigma, St Louis Mo.).

A glioblastoma cell line, GBM-18, was maintained in DME supplemented with 5% calf serum, 1 mM L-glutamine, and antibiotics.

A stable 3T3 line secreting the soluble chimeric protein, mouse FLK1:SEAPs (secretory alkaline phosphastase), was generated and maintained in DMEM and 10% calf serum. Conditioned media was collected. Soluble FLK-1:SEAP is isolated from the conditioned media.

Example II. Isolation of Monoclonal Antibodies

Example II-1. Rat anti mouse FLK-1 monoclonal antibody DC101 (IgG1)

Lewis rats (Charles River Labs) were hyperimmunized with an immune complex consisting of the mouse FLK-1:SEAPs soluble receptor, a rabbit anti-alkaline phosphatase polyclonal antibody and Protein-G sepharose beads. The animals received 7 intraperitoneal injections of this complex spread over three months (at days 0, 14, 21, 28, 49, 63, 77). At various times, the animals were bled from the tail vein and immune sera screened by ELISA for high titer binding to mFLK-1:SEAPs. Five days after the final injection, rats were sacrificed and the spleens aseptically removed. Splenocytes were washed, counted, and fused at a 2:1 ratio with the murine myeloma cell line NS1. Hybridomas were selected in HAT medium and colonies screened by ELISA for specific binding to mFLK-1:SEAPs but not the SEAPs protein. A number of positive hybridomas were expanded and cloned three times by limiting dilution. One subclone, designated DC101, was further characterized.

Example II-2. Mouse anti mouse FLK-1 monoclonal antibodies Mab 25 and Mab 73

Murine anti-FLK-1 monoclonal antibodies (Mabs) were produced using a similar protocol as that employed for DC101. Briefly, mice were injected with a complex of FLK-1/SEAP soluble receptor bound to either an anti-SEAP-Protein/A Sepharose complex or wheat germ agglutinin Sepharose from conditioned medium of transfected NIH 3T3 cell. Mice were hyperimmunized at periodic intervals over a 6 month period. Immune splenocytes were pooled and fused with the murine myeloma cell line, NSI. Hybridomas were selected in HAT medium and following incubation, colonies were screened for mouse Mab produciton. Unlike the protocol employed for DC101, positive supernatants were initially screened for binding to the FLK-1/fms receptor captured from C441 cell lysates on ELISA plates coated witha peptide generated polyclonal antibody against the C-terminal region of fms. Reactive Mabs were then assayed by ELISA for binding to intact C441 cells and to purified FLK-1/SEAP versus SEAP alone. The supernatants from hybridomas showing binding to C441 and reactivity with FLK-I/SEAP but not SEAP were expanded, grown in ascites, and purified (EZ-PREP, Pharmacia). Purified Mabs were subjected to assays on C441 cells to determine their cell surface binding by FACS and their ability to inhibit VEGF induced activation of FLK-1/fms in phosphorylation assays. The results of these studies led to the cloning of Mabs 25 and 73 (isotype IgG1) for further characterization based on their capabilities to bind specifically to FLK-1 and block receptor activation at levels comparable to that observed for DC101.

Example III. ASSAYS

Example III-1. ELISA Methods

Antibodies were screened by a solid state ELISA in which the binding characteristics of the various mAbs to FLK-1:SEAP and SEAP protein were compared. Microtiter plates were coated with 50–100 ng/well of either FLK-1:SEAP or AP in pH9.6 carbonate buffer overnight at 4° C. Plates were blocked with phosphate buffered saline supplemented with 10% new born calf serum (NB10) for one hour at 37° C. Hybridoma supernatants or purified antibodies were added to the plates for two hours at 37° C. followed by goat anti-rat IgG conjugated to horse radish peroxidase (Tago) added for an additional hour at 37° C. After extensive washing, TMB (Kirkegaard and Perry, Gaithersburg Md.) plus hydrogen peroxide was added as the chromogen and the plates read at 450 nm in an ELISA reader.

Example III-2. Isotyping

Isotyping of the various monoclonal antibodies was done as previously described (Songsakphisarn, R. and Goldstein, N .I., Hybridoma 12: 343–348,1993) using rat isotype specific reagents (Zymed Labs, South San Francisco Calif.).

Example III-3. Phosphorylation. Immunoprecipitation and Immunoblot Assays

The phosphorylation assays and Western blot analysis with C441 and 10A2 cells were performed as previously described (Tessler et al., 1994) with some modifications. Briefly, cells were grown to 90% confluency in DME-10% CS and then serum starved in DME-0.5% CS for 24 hours prior to experimentation. HUVEC cells were grown to subconfluence in EGM basal media. For neutralization assays, cells were stimulated with various concentrations of the appropriate ligand under serum free conditions (DME −0.1% BSA) in the presence and absence of mAb DC101 for 15 minutes at room temperature. The ligands, VEGF and CSF-1, were assayed at concentrations of 10–80 ng/ml and 20–40 ng/ml, respectively. Monoclonal antibodies were assayed at concentrations ranging from 0.5 ug/ml to 10 ug/ml. To evaluate the effects of mAb DC101 on the VEGF induced activation of the FLK-1-fms receptor, antibody was either added simultaneously (competitive inhibition) or pre-bound to cells for 15 minutes at room temperature prior to the addition of ligand. Cells incubated in serum free medium in the absence and presence of DC101 served as controls for receptor autophosphorylation in the absence of ligand and the presence of antibody, respectively. A control cell line expressing the fms/FLK2 chimeric receptor (10A2) was starved and stimulated with 20 and 40 ng/ml CSF-1 and assayed in the presence and absence of 5 ug/ml DC101.

Following stimulation, monolayers were washed with ice cold PBS containing 1 mM sodium orthovanadate. Cells were then lysed in lysis buffer (20 mM Tris-HCl, pH 7.4, 1% Triton X-100, 137 mM NaCl, 10% glycerol, 10 mM EDTA, 2 mM sodium orthovanadate, 100 mM NaF, 100 mM sodium pyrophosphate, 5 mM Pefabloc (Boehringer Mannheim Biochemicals, Indianapolis Ind.), 100 ug aprotinin and 100 ug/ml leupeptin) and centrifuged at 14000 ×g for 10 minutes. Protein was immunoprecipitated from cleared lysates of transfected cells using polyclonal antibodies generated to peptides corresponding to the C-terminal region of the human fms receptor (Tessler et al., J. Biol. Chem. 269, 12456–12461, 1994) or the murine FLK-2 interkinase domain (Small et al., Proc. Natl. Acad. Sci. USA, 91, 459–463, 1994) coupled to Protein A Sepharose beads. Where indicated, immunoprecipitations with DC101 or irrelevant rat IgG were performed with 10 ug of antibody coupled to Protein G beads. The beads were then washed once with 0.2% Triton X-100, 10 mM Tris-HCl pH8.0, 150 mM NaCl, 2 mM EDTA (Buffer A), twice with Buffer A containing 500 mM NaCl and twice with Tris-HCl, pH 8.0. Drained beads were mixed with 30 ul in 2×SDS loading buffer and subjected to SDS PAGE in 4–12% gradient gels (Novex, San Diego Calif.). After electrophoresis, proteins were blotted to nitrocellulose filters for analysis. Filters were blocked overnight in blocking buffer (50 mM Tris-HCl, pH7.4, 150 mM NaCl (TBS) containing 5% bovine serum albumin and 10% nonfat dried milk (Biorad, Calif.). To detect phosphorylated receptor, blots were probed with a monoclonal antibody directed to phosphotyrosine (UBI, Lake Placid, NY) in blocking buffer for 1 hour at room temperature. Blots were then washed extensively with 0.5× TBS containing 0.1% Tween-20 (TBS-T) and incubated with goat anti-mouse Ig conjugated to horseradish peroxidase (Amersham). Blots were washed with TBS and incubated for 1 minute with a chemiluminescence reagent (ECL, Amersham). Anti-phosphotyrosine reacting with phosphorylated proteins was detected by exposure to a high performance luminescence detection film (Hyperfilm-ECL, Amersham) for 0.5 to 10 minutes.

To detect FLK-1/fms in C441 cells receptor levels, blots were stripped according to manufacturer's protocols (Amersham) and reprobed with the anti-fms rabbit polyclonal antibody.

Example III-4. Flow Cytometer Binding Assays

C441 cells were grown to near confluency in 10 cm plates. Cells were removed with a non-enzymatic dissociation buffer (Sigma), washed in cold serum free medium and resuspended in Hanks balanced salt solution supplemented with 1% BSA (HBSS-BSA) at a concentration of 1 million cells per tube. mAb DC101 or an isotype matched irrelevant antibody anti FLK-2 23H7 was added at 10 ug per tube for 60 minutes on ice. After washing, 5 ul of goat anti-mouse IgG conjugated to FITC (TAGO) was added for an additional 30 minutes on ice. Cells were washed three times, resuspended in 1 ml of HBSS-BSA, and analyzed on a Coulter Epics Elite Cytometer. Non-specific binding of the fluorescent secondary antibody was determined from samples lacking the primary antibody.

Example III-5. Binding Assays to Intact Cells

Assays with C441 cells were performed with cells grown to confluency in 24 well dishes. HUVEC cells were grown to confluency in 6 well dishes. Monolayers were incubated at 4° C. for 2 hours with various amounts of mAb DC101 in binding buffer (DMEM, 50 Mm HEPES pH 7.0, 0.5% bovine serum albumin). Cells were then washed with cold phosphate buffered saline (PBS) and incubated with a secondary anti-rat IgG antibody conjugated with biotin at a final concentration of 2.5 ug/ml. After 1 hour at 4° C cells were washed and incubated with a streptavidin-horse radish peroxidase complex for 30 minutes at 4° C. Following washing, cell-bound antibody was determined by measuring the absorbance at 540 nm obtained with a colormetric detection system (TMB, Kirkegaard and Perry). The OD 540 nm of the secondary antibody alone served as the control for non-specific binding.

Example III-6. Cell proliferation assays

Mitogenic assays were performed using the Cell Titer 96 Non Radioactive Cell Proliferation Assay Kit (Promega Corp., Madison, Wis.). In this assay proliferation is measured color metrically as the value obtained from the reduction of a tetrazolium salt by viable cells to a formazan product. Briefly, HUVEC cells were grown in 24 well gelatin-coated plates in EGM basal media at 1000 cells/well. After a 48-hour incubation various components were added to the wells. VEGF was added at 10 ng/ml to the media in the presence and absence of 1 ug/ml of mAb DC101. Where indicated, heparin (Sigma) was added to a final concentration of 1 ug/ml. Cells were then incubated for an additional 3 days. To measure cell growth, a 20 ul aliquot of tetrazolum dye was added to each well and cells were incubated for 3 hrs at 37° C. Cells were solubilized and the absorbance (OD570) of the formazan product was measured as a quantitation of proliferation.

Example IV. IN VITRO ACTIVITY ASSAYS

Example IV-1. Murine anti-FLK-1 Mabs 25 and 73 elicit a specific neutralization of VEGF induced activation of the FLK-1/fms receptor Assays were performed with immunoprecipitated FLK/fms and PDGF receptors from equal concentrations of the FLK-1/fms transfected 3T3 cell line, C441 whereas the human EGFR was immunoprecipitated from the tumor cell line, KB. Cells were stimulated with RPMI-0.5% BSA containing 20 ng/ml VEGF (FLK-1/fms), DMEM-10% calf serum (PDGFR), or 10 ng/ml EGF (EGFR), in the presence and absence of 10 ug/ml of the murine anti-FLK-1 Mabs, 25 and 73. Following stimulation, cells were washed with PBS-1 mM sodium orthovanadate and lysed. FLK-1/fms and PDGFR were immunoprecipitated from lysates with peptide generated polyclonal antibodies against the C-terminal region of the c-fms (IM 133) and the PDGF (UBI) receptors, respectively. EGFR was immunoprecipitated with a Mab (C225) raised against the N-terminal region of the human receptor. Immunoprecipitated lystates were subjected to SDS polyacrylamide electrophoresis followed by western blotting. Blots were probed with an anti-PTyr Mab (UBI) to detect receptor activation. Receptor neutralization of stimulated cells was assessed relative to an irrelevant Mab and the unstimulated control.

Example IV-2. Detection of the FLK-1/fms receptor by western blotting using Mab 25 and Mab 73 as probes Receptor was detected by the murine anti-FLK-1 Mabs on western blots of the FLK1/fms receptor immunoprecipiated by a peptide generated polyclonal antibody against the C-terminal region of the c-fms receptor from lysated prepared from equal concentrations of transfected 3T3 cell line C441. Following analysis by SDS gel electrophoresis and western blotting, the blot was divided into four parts and each section was probed with 50 ug/ml of the anti-FLK-1 Mabs 25 and 73. Blots were then stripped and reprobed with the anti-fms polyclonal antibody to verify that the bands deted by each Mab represented the FLK-1/fms receptor.

Example IV-3. Detection of activated KDR from VEGF stimulated HUVEC and OVCAR-3 cells by immunoprecipiation with anti-FLK-1 Mabs Proteins were immunoprecipitated by different antibodies from a lysate of freshly isolated HUVEC. Prior to lysis, cells were stimulated with 20 ng/ml VEGF for 10 minutes at room temperature in RPMI-0.5% BSA and washed with PBS containing 1 mM sodium orthovanadate. Individual immunoprecipitations were performed with equal volumes of lysate and then subjected to SDS polyacrylamide electrophoresis followed by western blotting. The blot was probed initially with an anti-PTyr Mab (UBI) and then sequentially stripped and reprobed with a peptide generated polyclonal antibody against the interkinase of FLK-1/KDR (IM 142), followed by a polyclonal antibody against the C-terminal region of FLT-1 (Santa Cruz Biotechnology, Inc). The immunoprecipitations were performed with an irrelevant rat Mab, 23H7, an irrelevant mouse Mab, DAB 8, versus the anti-FLK-1 Mabs, DC1 01, 73, 25 and an anti-FLK-1/KDR polyclonal antibody, IM 142. In some cases blots were stripped and reprobed with the anti-FLK-1 Mabs 73 and 25 to detect cross reactive bands.

A similar protocol was employed to detect KDR receptor form(s) in the ovarian carcinoma cell line OVCAR-3.

Example V. ACTIVITY OF ANTIBODIES

Example V-1. ELISA and Immunoprecipitation with DC101

Rat lgG1 monoclonal antibody DC101 was found to be specific for the murine tyrosine kinase receptor FLK-1. ELISA data showed that the antibody bound to purified FLK-1:SEAP but not alkaline phosphatase or other receptor tyrosine kinases such as FLK-2. As seen in FIG. 1, DC101 immunoprecipitates murine FLK1:SEAPS but not SEAPS alone.

Example V-2. INHIBITION OF FLK-1 RECEPTOR PHOSPHORYLATION WITH

Figure 2A:
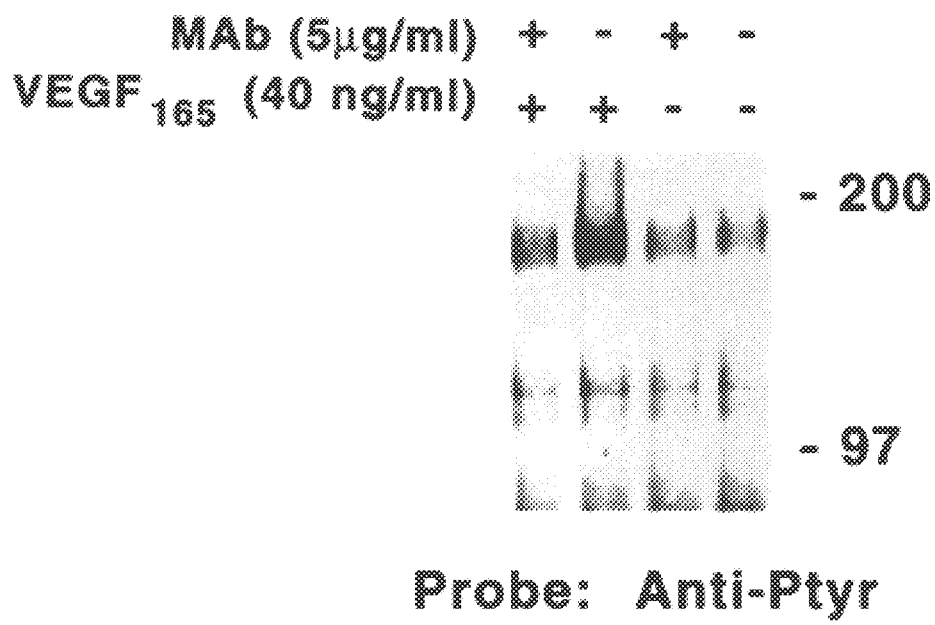
FIGS. 2A and 2B.
Figure 2B:
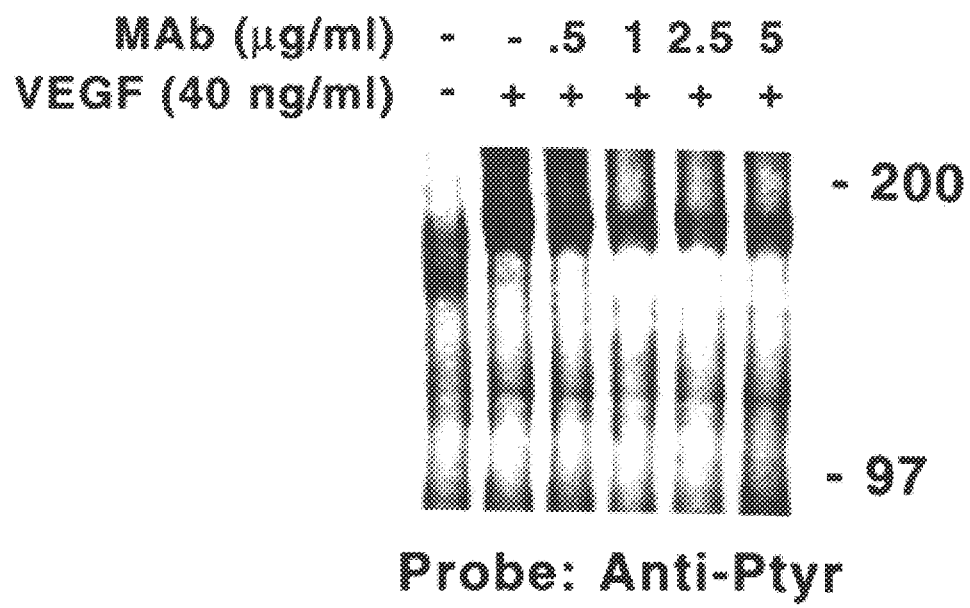
Figure 3A:
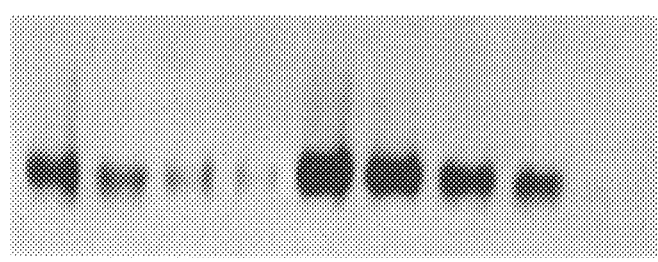
FIGS. 3A and 3B.
Figure 3B:
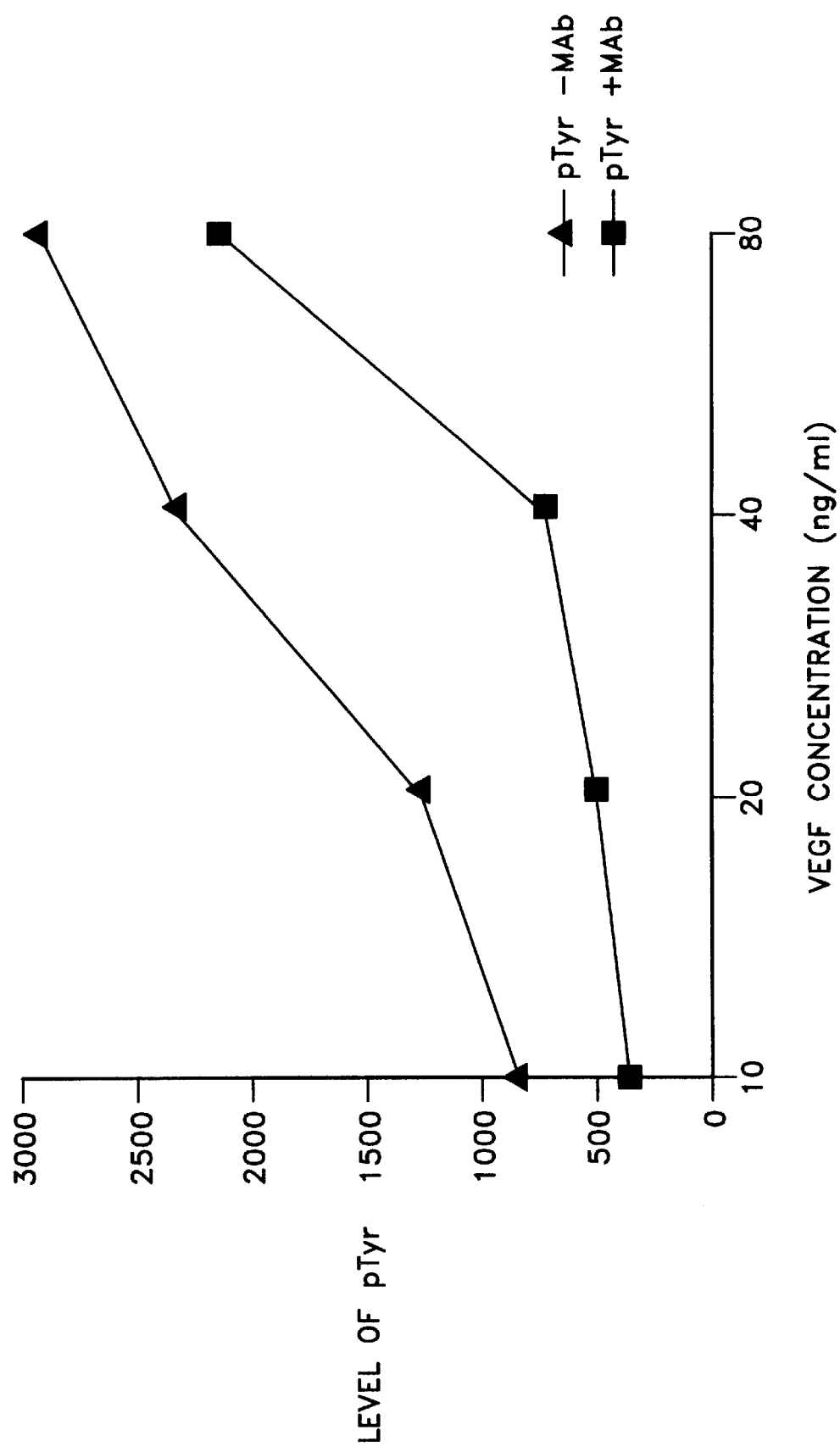

Experiments were then performed to determine whether DC101 could neutralize phosphorylation of FLK1 in C441 cells by its cognate ligand, $VEGF_{165}$. In these studies, monoclonal antibody and VEGF were added simultaneously to monolayers for 15 minutes at room temperature. These conditions were designed to determine the competitive effects (competitive inhibition) of the antibody on receptor/ligand binding. The results of these assays, shown in FIG. 2A, indicate that $VEGF_{165}$ induced phosphorylation of the FLK1/fms receptor was markedly reduced when cells were assayed in the presence of DC101. In addition, these data suggest that the Mab competes with $VEGF_{165}$ to prevent a full activation of receptor by ligand. To determine the sensitivity of the VEGF-FLK1 interaction to inhibition by DC101, C441 cells were assayed at maximal stimulatory concentrations of $VEGF_{165}$ (40 ng/ml) combined with varying levels of the antibody. The results of these Mab titrations are shown in FIG. 2B. A marked decrease in the phosphorylation of FLK1 by $VEGF_{165}$ was observed when DC101 was included at concentrations greater than 0.5 ug/ml. These data show that relatively low concentrations of antibody (<1 ug/ml) are sufficient to inhibit receptor activation by ligand. At 5 ug/mi the antibody is able to neutralize $VEGF_{165}$ stimulation of FLK1 in the presence of excess ligand at 80 ng/ml (FIGS. 3A and 3B). As a control, the effect of DC101 was tested on the fully stimulated fms/FLK2 receptor (10A2 cell line) using CSF-1. Underthese conditions, DC101 showed no effect on receptor activation.

Example V-3. Inhibition studies with DC101

Figure 4:
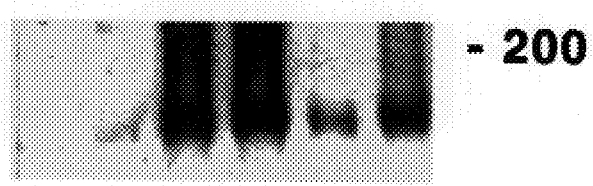
FIG. 4: Inhibition of VEGF-FLK-1/fms activation by prebound mAb DC101. C441 cells were stimulated with the concentrations of VEGF indicated in the absence (Lanes 3 and 4) and presence (Lanes 5 and 6) of DC101. Unstimulated cells (Lanes 1 and 2) serve as controls. MAb was assayed using two sets of conditions. For P, cells were prebound with Mab followed by stimulation with VEGF for 15 minutes at room temperature. For C, MAb and ligand were added simultaneously and assayed as above.

The extent and specificity of Mab inhibition was further assessed by studies in which DC101 was preincubated with cells before the addition of ligand to allow maximal interaction of antibody with receptor. In these experiments, monolayers were incubated with 5 ug/ml of DC101, a rat anti-FLK2 Mab (2A13) prepared by conventional techniques (ImClone, NY), and control rat IgG1 (Zymed Labs) for 15 minutes at room temperature prior to the addition of 40 ng/ml of $VEGF_{165}$ for an additional 15 minutes. For comparison, assays were run in which DC101 and $VEGF_{165}$ were added simultaneously (competitive inhibition). The results of these studies (FIG. 4) show that preincubation of the anti-FLK-1 monoclonal antibody with FLK1/fms transfected cells completely abrogates receptor activation by $VEGF_{165}$. Similar results were observed using $VEGF_{121}$ for stimulation. While phosphorylation of FLK1 by VEGF is not affected by the addition of irrelevant isotype matched rat antibodies, the reactivity of the same blot probed with the anti-fms polyclonal antibody shows an equal level of receptor protein per lane. These data indicate that the inhibition of phosphorylation observed with DC101 was due to the blockage of receptor activation rather than a lack of receptor protein in the test samples.

Example V-4. Binding of DC101 to C441 cells by FACS analysis

Figure 6:
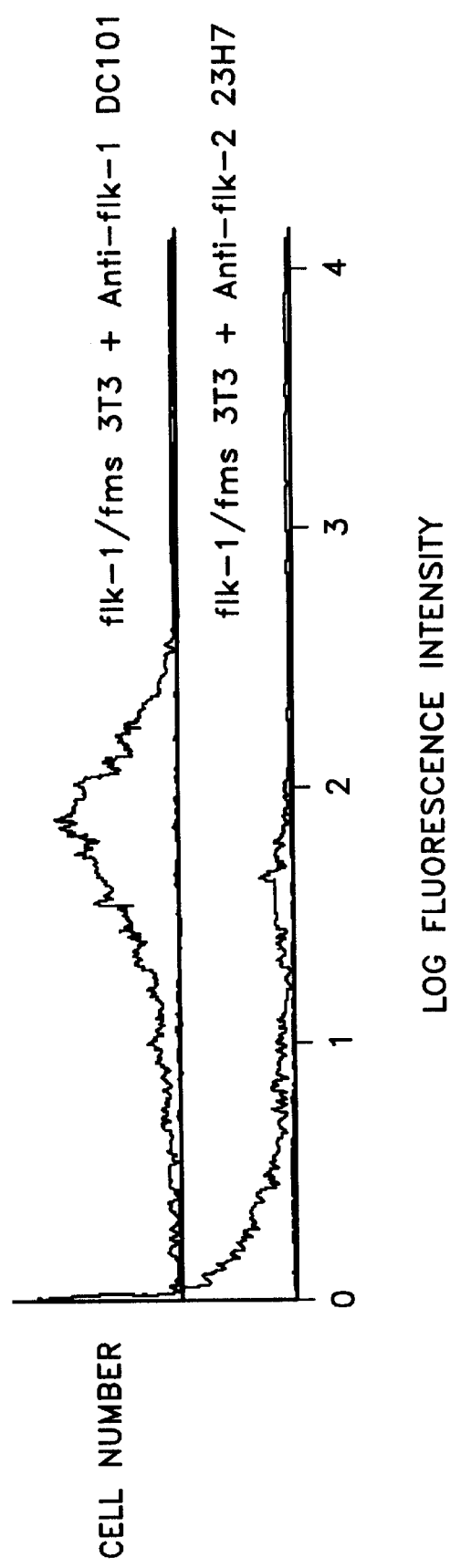
FIG. 6: FACS analysis of anti-FLK-1 mAb binding to FLK-1/fms transfected 3T3 Cells (C441). Transfected FLK-1/fms 3T3 cells were incubated on ice for 60 minutes with 10 ug/ml of the anti-FLK-1 MAb DC101 or the isotype matched irrelevant anti-FLK-1 MAb 23H7. Cells were washed and reincubated with 5 ug of goat anti-mouse lgG conjugated to FITC, washed, and analyzed by flow cytometry to determine antibody binding. Data shows the level of fluorescence for DC101 to C441 cells relative to that detected with the irrelevant MAb 23H7.
Figure 7:
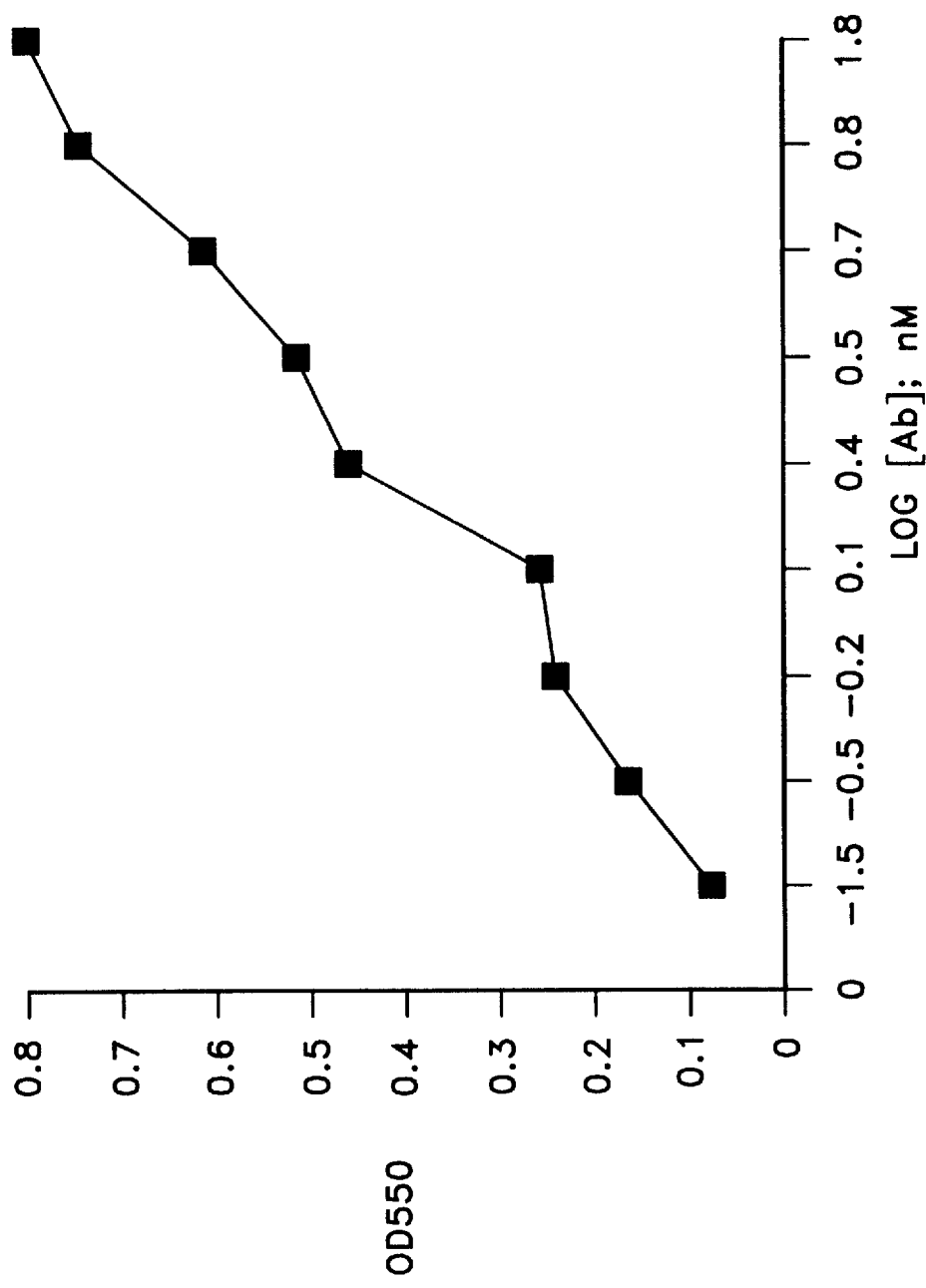
FIG. 7: Saturation binding of mAb DC101 to the FLK-1/fms receptor on the transfected 3T3 cell line C441. Confluent C441 cells were incubated in 24 well plates with increasing concentrations of MAb DC101 (50 ng/ml to 2 ug/ml) for two hours at 4° C. Cells were washed and incubated with 5 ug anti-rat IgG-biotin conjugate. To detect binding, cells were washed, incubated with a 1:1000 dilution of streptavidin-HRP, washed and incubated in a colormetric detection system (TMB). Data represents the absorbance at 540 nm versus increasing concentrations of MAb DC101. The binding of the secondary antibody to cells alone was subtracted from each determination to adjust for non-specific binding. Data represents the average of three independent experiments.

The mAb was assayed by FACS analysis for binding to 3T3 cells transfected with the FLK-1/fms receptor (C441 cells). The results, shown in FIG. 6, demonstrate that the chimeric FLK-1/fms expressed on the surface of C441 cells is specifically recognized by mAb DC101 and not by an antibody of the same isotype raised against the related tyrosine kinase receptor, FLK-2. The efficacy of the mAbreceptor interaction at the cell surface was determined from assays in which varying levels of mAb binding was measured on intact C441 cells. These results, shown in FIG. 7, indicate that mAb binds to the FLK-1/fms receptor with a relative apparent affinity of approximately 500 ng/ml. These results indicate that the mAb has a strong affinity for cell surface expressed FLK-1.

Example V-5. Reactivity of DC101 by Immunoprecipitation

Figure 8:
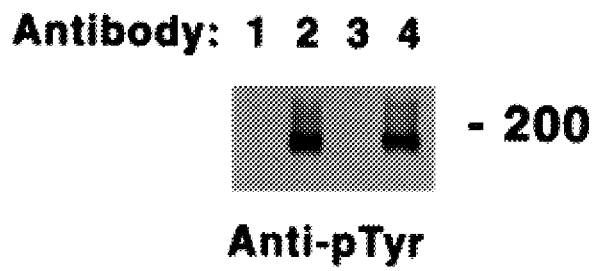
FIG. 8: Immunoprecipitation of phosphorylated FLK-1/fms from VEGF stimulated FLK-1/fms transfected 3T3 cells. Cells were stimulated with VEGF as described in the Experimental Procedures and lysates were immunoprecipitated with irrelevant or relevant antibodies as follows: 1. rat anti-FLK2 lgG2a (Mab 2A13); 2. rat anti-FLK-1 lgG1 (Mab DC101); 3. rat anti-FLK2 lgG1 (Mab 23H7); 4. rabbit anti-fms polyclonal antibody. Immunoprecipitated protein was subjected to SDS PAGE followed by Western blotting. The immunoprecipitation of VEGF activated receptor was detected by probing the blots with an anti-phosphotyrosine antibody.
Figure 9:
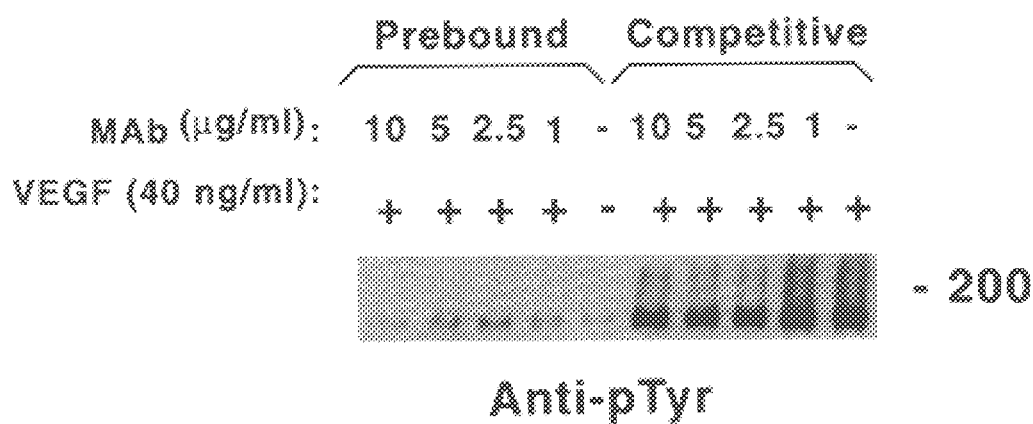
FIG. 9: Sensitivity of VEGF-induced phosphorylation of the FLK-1/fms receptor to inhibition by mAb DC101. Prebound and competitive assays were performed with 40 ng/ml of VEGF at the antibody concentrations indicated. Cell lysates were prepared for receptor detection with anti-phophotyrosine as described in the Examples below.

The extent of DC101 reactivity with the FLK-1/fms receptor was further assessed by determining the capacity of the antibody to immunoprecipitate the receptor following activation by VEGF. FIG. 8 shows an immunoprecipitation by mAb DC101 of the phosphorylated FLK-1/fms receptor from VEGF stimulated C441 cells. The results show that the DC101 monoclonal and anti-fms polyclonal antibodies display similar levels of receptor interaction while rat anti FLK-2 antibodies 2H37 (IgG1) and 2A13 (IgG2a) show no reactivity. Experiments were then performed to determine whether mAb DC101 could neutralize the VEGF induced phosphorylation of FLK-1/fms at maximal stimulatory concentrations of ligand (40 ng/ml). In these studies, monoclonal antibody was added to monolayers either simultaneously with ligand or prior to ligand stimulation and assayed for 15 minutes at room temperature. These conditions were studied to determine both the competitive effects (competitive inhibition) of the antibody on receptor/ligand binding as well as the efficacy of prebound antibody to prevent receptor activation. The results of these assays, shown in FIG. 4, indicate that phosphorylation of the FLK-1/fms is reduced by the simultaneous addition of mAb with VEGF and markedly inhibited by antibody prebound to the receptor. A densitometry scan of these data revealed that mAb DC101 interacts with FLK-1/fms to inhibit phosphorylation to a level that is 6% (lane 5, P) and 40% (lane 6,C)

of the fully stimulated receptor control (lane 4). From these data we infer that mAb DC101 strongly competes with the ligand-receptor interaction to neutralize FLK-1 receptor activation. To determine the sensitivity of the VEGF-FLK-1 interaction to inhibition by mAb DC101, C441 cells were assayed with maximal VEGF levels in the presence of increasing concentrations of antibody. Assays were performed with the mAb under competitive and prebinding conditions. The results of these mAb titrations are shown in FIG. 9. A marked decrease in the phosphorylation of FLK-1 is observed when mAb DC101 competes with VEGF antibody at concentrations greater than 0.5 ug/ml. These data also show that relatively low concentrations of prebound antibody (<1 ug/ml) are sufficient to completely inhibit receptor activation by ligand.

Example V-6. Activity of DC101 by phosphorylation assay

Figure 10:
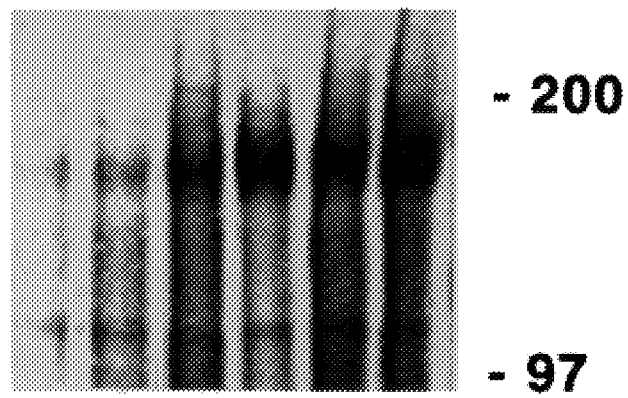
FIG. 10: Effect of mAb DC101 on CSF-1 induced phosphorylation of the FMS receptor. In (B), the fms/FLK-2 transfected 3T3 cell line, 10A2, was stimulated with optimal stimulatory levels of CSF-1 in the absence (Lanes 3 and 4) and presence (Lanes 5 and 6) of 5 ug/ml of MAb DC101. Unstimulated cells assayed in the absence (Lane 1) or presence (Lane 2) of antibody serve as controls. Cell lysates were prepared for detection by anti-phosphotyrosine as described in the Examples below.

To further evaluate the antagonistic behavior of mAb DC101 on receptor activation, phosphorylation assays were performed in which a fixed amount of antibody (5 ug/ml) was added to C441 cells stimulated with increasing amounts of ligand (FIG. 3A). The level of phosphorylation induced by each ligand concentration in the presence and absence of mAb DC101 was also quantitated by densitometry readings. The plot of these data given in FIG. 3B indicates that the antibody was able to partially neutralize receptor phosphorylation even in the presence of excess amounts of VEGF. To evaluate the specificity of mAb DC101 on receptor activation, the antibody was tested for its ability to competitively inhibit CSF-1 induced activation of the fms/FLK-2 receptor in the 3T3 transfected cell line, 10A2. In these experiments 5 ug/ml of mAb DC101 was tested together with CSF-1 concentrations (20–40 ng/ml) that are known to result in full activation of the receptor. These results, which are shown in FIG. 10, indicate that mAb DC101 has no effect on the CSF-1 mediated phosphorylation of the fms/FLK-2 receptor.

Example V-7. DC101 inhibition by pre-incubation studies

Figure 11:
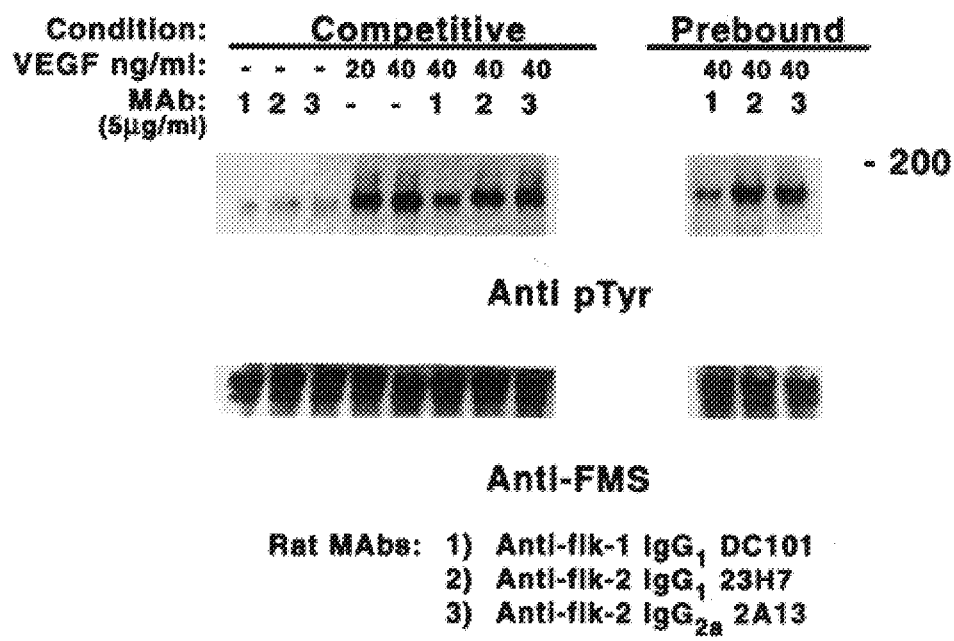
FIG. 11: Specificity of mAb DC101 neutralization of the activated FLK-1/fms receptor. C441 cells were stimulated with 20 or 40 ng/ml of VEGF in the presence of DC101 (IgG1) or the irrelevant anti-FLK-2 rat monoclonal antibodies 2A13 (IgG2a) or 23H7 (IgG1). Assays were performed with each antibody in the absence of VEGF (Lanes 1 to 3) and in the presence of VEGF under competitive (lanes 4 to 8) or prebound (lanes 9 to 11) conditions. Cell lysates were prepared for detection by anti-phosphotyrosine as described in the Examples below. Blots were stripped and reprobed to detect the FLK-1/fms receptor using a rabbit polyclonal antibody to the C-terminal region of the fms receptor.

The extent and specificity of antibody inhibition was further assessed by studies in which DC101 or an irrelevant antibodies were preincubated with cells before the addition of ligand to assure maximal interaction of antibody with receptor. In these experiments, monolayers were preincubated with either 5 ug/ml of DC101, a rat anti-FLK2 mAb (2A13) or a control rat IgG1 (Zymed Labs) prior to the addition of 40 ng/ml of VEGF. For comparison, competitive assays were run in which antibodies and VEGF were added simultaneously. The results of these studies show that only the preincubation of the anti-FLK-1 monoclonal antibody with FLK1/fms transfected cells completely abrogates receptor activation by VEGF while phosphorylation of FLK1 by VEGF is not affected by the addition of irrelevant isotype matched rat antibodies. The reactivity of the same blot probed with the anti-fms polyclonal (FIG. 11) shows an equal level of receptor protein per lane. These data indicate that the lack of phosphorylation observed with mAb DC101 treated cells was due to the blockage of a VEGF-induced phosphorylation of equal amounts of expressed receptor.

Example V-8. Interaction of antibodies with homologous receptor forms

Figure 13:
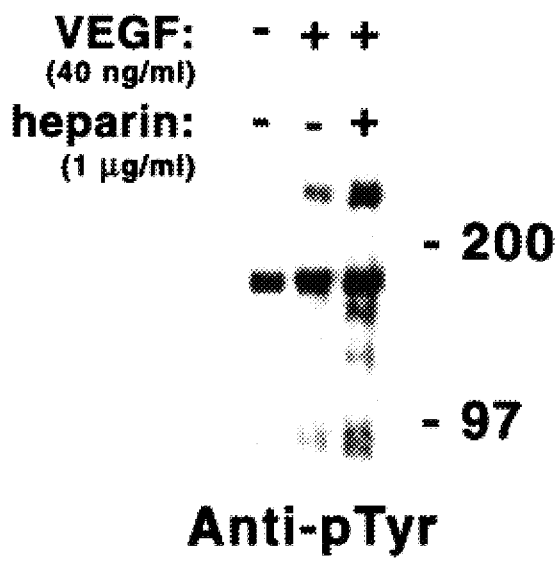
FIG. 13: Immunoprecipitation of phosphorylated receptor bands from VEGF stimulated HUVEC cells. HUVEC cells were grown to subconfluency in endothelial growth medium (EGM) for three days without a change of medium. Receptor forms were immunoprecipated by MAb DC101 from lysates of unstimulated cells (Lane 1), VEGF stimulated cells (lane 2), and cells stimulated with VEGF in the presence of 1 ug/ml heparin (Lane 3). Phosphorylation assays, immunoprecipitations, and detection of the phosphorylated receptor forms were performed as described in the Experimental Procedures.
Figure 14:
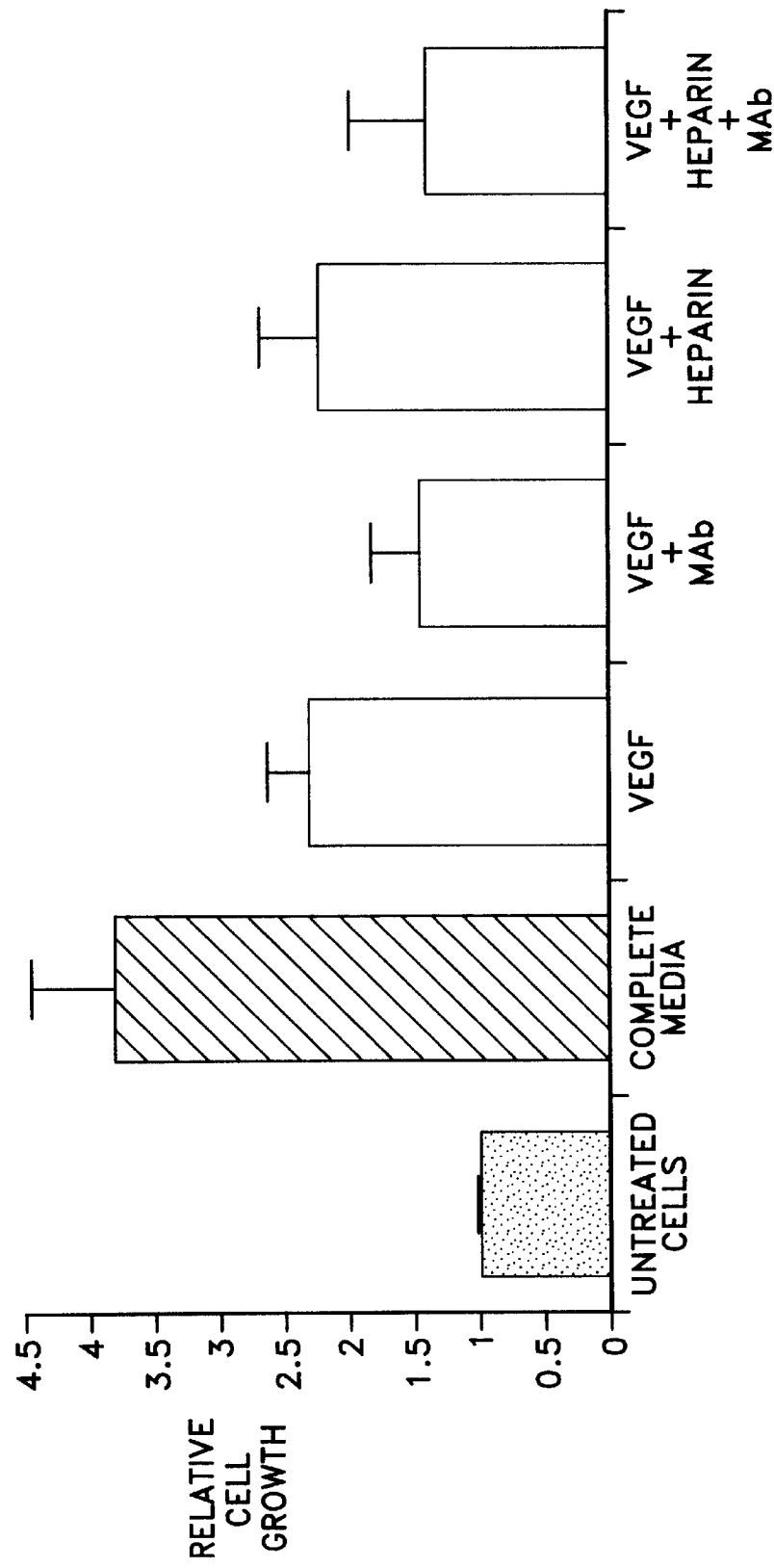
FIG. 14: Effect of mAb DC101 on the proliferation of HUVEC cells in response to VEGF. Cells were grown for 48 hours as described in the legend to FIG. 6. Cells were then subjected to the following assay conditions: no addition to medium (untreated); a change of fresh endothelial growth medium (complete medium); the addition of 10 ng/ml of VEGF in the absence or presence of 1 ug/ml heparin; and VEGF and VEGF-heparin treated cells assayed in the presence of 1 ug/ml of DC101. Cells were assayed for proliferation by colormetric detection at 550 nm using a cell proliferation assay kit (Promega).

Experiments were then conducted to determine whether the anti FLK-1 monoclonal antibodies interact with homologous receptor forms on human endothelial cells. A titration of increasing concentrations of DC101 on cloned HUVEC cells (ATCC) indicated that the antibody displayed a complex binding behavior. The data represent differential antibody interactions with VEGF receptors reported to occur on endothelial cells (Vaisman et al., J. Biol. Chem. 265, 19461–19466, 1990). The specificity of DC101 interaction with VEGF stimulated HUVEC cells was then addressed using phosphorylation assays under similar conditions as those reported for FIG. 8. In these studies DC101 immunoprecipitates protein bands from HUVEC cells that have molecular weights similar to those reported for cross linked VEGF-receptor bands when the ligand component is subtracted (FIG. 13). These bands display an increased phosphorylation when cells are stimulated by VEGF (compare lanes 1 and 2 in FIG. 13). In addition, the VEGF induced phosphorylation of the receptor bands is potentiated by the inclusion of 1 ug/ml heparin in the assay (lane 3 in FIG. 13). These findings are consistent with previous reports of increased VEGF binding to endothelial cells in the presence of low concentrations of heparin (Gitay-Goren et al., J. Biol. Chem. 267, 6093–6098.1992).

It is difficult to ascertain which immunoprecipitated protein interacts with DC101 to generate the complex of phosphorylated bands observed in FIG. 13 given the various receptor forms shown to bind VEGF on HUVEC and the possibility of their association upon stimulation. Cell surface expressed receptor forms with molecular weights of approximately 180 (KDR), 155, 130–135, 120–125 and 85 have been reported to bind VEGF on HUVEC. Such findings address the possibility that several different receptor forms may heterodimerize upon ligand stimulation in a manner similar to that reported for KDR-FLT-1. However, with the exception of KDR, the exact nature and role of these receptor forms have yet to be defined. Consequently, antibody reactivity may result from interaction(s) with one of several VEGF receptors independent of KDR.

DC101 does not react with human KDR in an ELISA format nor bind to freshly isolated HUVEC by FACS analysis. These results suggest that a direct interaction of DC101 with human KDR is highly unlikely.

Unlike DCl01, Mab 25 and Mab 73 both react with human KDR in an ELISA format and bind to freshly isolated HUVEC by FACS analysis.

Example V-9. Mitogenic assays of HUVEC.

An inhibitory effect of DC101 on endothelial cells was observed when the antibody was tested in mitogenic assays of HUVEC cells (ATCC) stimulated with VEGF in the presence and absence of antibody (FIG. 13). These results show that a marked increase in cell proliferation by VEGF is reduced approximately 35% by DC101. Heparin shows no differential effect on cell growth under the growth conditions employed in these assays.

Since DC101 can exert effects on VEGF induced proliferation and receptor phosphorylation of HUVEC it is conceivable that these results are due to a Mab interaction with an undefined receptor form which is poorly accessible at the cell surface, but which plays some role, albeit minor, in HUVEC growth. Also, the immunoprecipitation of phosphorylated bands of the correct molecular weight by DC101 from VEGF stimulated HUVEC also supports the notion that DC101 may interact with an undefined FLK-1 like protein that associates with an activated receptor complex.

Example V-10. Binding of Mab 25 and Mab 73 to C441 cells and HUVEC

Mabs 25 and 73 bind to C441 and HUVEC by FACS analysis and show internalization in both cell lines. Results from western blots show that both anti-FLK-1 Mabs can detect the band(s) for the FLK/fms receptor in immunoprecipitates by an anti-fms polyclonal antibody from C441 cells. (See example IV-2 above for protocol.) These antibodies elicit a specific neutralization of VEGF induced activation of the FLK-1/fms receptor and have no effect on the phosphorylation of the mouse PDGF receptor by PDGF or the human EGF receptor by EGF. (See example IV-1 above for protocol.) They have the capacity to inhibit VEGF stimulated HUVEC in proliferation assays to 50% whereas DC101 affects growth to a far lesser extent.

Example V-11. Immunoprecipitation of KDR with Mab25 and Mab73

KDR represents one of the phosphoproteins immunoprecipitated by the Mab25 and Mab 73 from activated HUVEC. KDR was detected in western blot and immunoprecipitation analyses using an anti-FLK-1/KDR polyclonal antibody (IM142) from VEGF-stimulated early passage HUVEC. Conversely, bands immunoprecipitated by these antibodies from VEGF-stimulated HUVEC are cross reactive with IM142 but not an anti-FLT-1 polyclonal antibody. These findings infer that the Mabs may affect the activity of KDR in HUVEC based on experimental evidence implicating KDR as the VEGF receptor responsible for the proliferative response in activated endothelial cells. (See example IV-3 above for protocol.)

Example VI. Presence of VEGF receptor forms on non-endothelial (tumor) cells

Several tumor lines were screened for protein reactivity with DC101 by immunoprecipitation and detection with antiphosphotyrosine. Immunoblots from the cell lines 8161 (melanoma) and A431 (epidermoid carcinoma) yielded phosphorylated bands with molecular weights of approximately 170 and 120 kD. These results indicate that a human VEGF receptor form is expressed in non-endothelial cells, such as tumor cells.

Similar experiments have shown that a KDR like receptor is expressed in an ovarian carcinoma cell line, OVCAR-3. These cells also appear to secrete VEGF. Phosphorylated bands are immunoprecipitated by an anti-KDR polyclonal antibody from VEGF-stimulated OVCAR-3 cells that are reactive with anti-FLK-1 Mabs by western blotting. Also, bands immunoprecipitated by the murine Mabs from these cells show cross reactivity with the same polyclonal antibody. Furthermore certain murine anti-FLK-1 Mabs elicit an inhibitory effect on these cells in proliferation assays. These results demonstrate nonendothelial expression (i.e. on tumor cells) of human VEGF receptor forms. The data from the phosphorylation and proliferation assays also suggest that VEGF can modulate receptor activity in an autocrine and paracrine manner during tumorigenesis. (See Example IV-3 above for protocol.) Example VII. IN VIVO STUDIES USING DC101 Example VII-1. inhibition in vivo of angiogenesis by dc101

Figure 5:
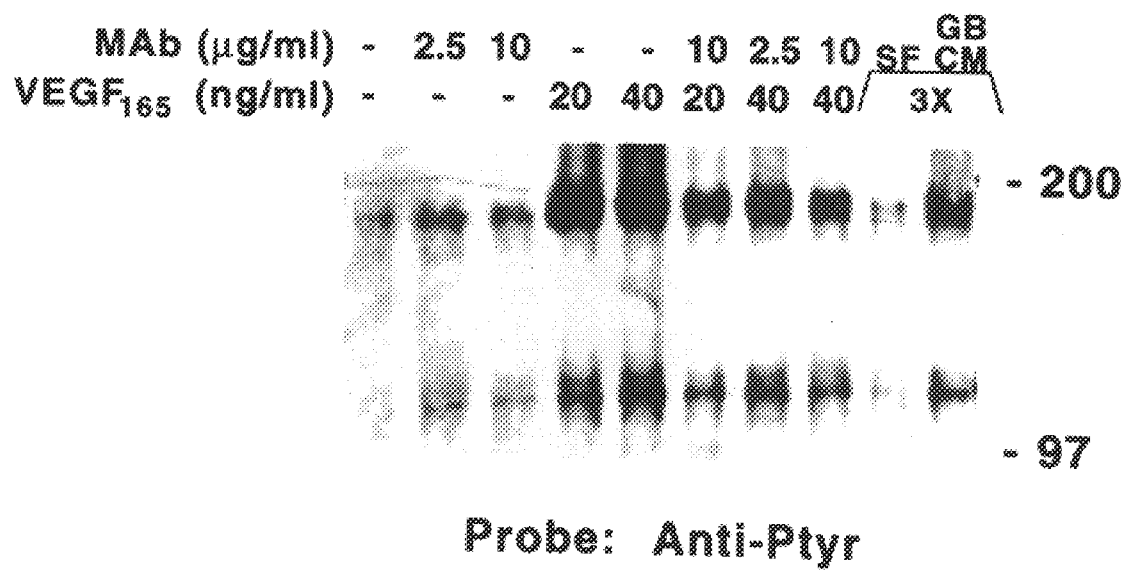
FIG. 5: VEGF-induced phosphorylation of the FLK-1/fms receptor by treatments with varying concentrations of monoclonal antibody DC101 and conditioned media from glioblastoma cells (GB CM).

In vivo studies were designed to determine if an anti-FLK1 monoclonal antibody would block the growth of VEGF-expressing tumor cells. In these experiments, a human glioblastoma multiform cell line was used that has high levels of VEGF message and secretes about 5 ng/ml of VEGF growth factor after a 24 hour conditioning in serum free medium (FIG. 5).

On day zero, athymic nude mice (nu/nu; Charles River Labs) were injected in the flank with 1–2 million glioblastoma cells. Beginning on the same day, animals received intraperitoneal injections of either DC101 and control antibodies (100 ug/animal). The mice received subsequent antibody treatments on days 3, 5, 7, 10, 12, 14, 17, 19, and 21. Animals received injections of 100 ug of either DC101 or a control rat antibody to the murine FLK2 (2A13) receptor on days 0, 3, 5, 7, 10, 12, 14, 17, 19, and 21 for a total inoculation of 1 mg/animal. Tumors began to appear by day 5 and followed for 50 days. Tumor size was measured daily with a caliper and tumor volume calculated by the following formula: p/6×larger diameter×(smaller diameter)$^2$ (Baselga J. Natl. Cancer Inst. 85: 1327–1333). Measurements were taken at least three times per week and tumor volume calculated as described above. One tumor bearing animal in the DC101 group died early in the study and was not used to determine statistical significance between the groups.

FIGS. 16A and 16B shows a comparison between the DC101 and the control 2A13 group of reduction in tumor growth over 38 days in individual animals. Although all animals developed tumors of varying sizes and number during the course of the study, DC101-treated mice showed an overall delay in tumor progression. One mouse in the DC101 group remained tumor free until day 49 when a small growth was observed. Even then, tumor growth was markedly suppressed. Statistical analysis of the data was done to assess differences in tumor size between the two groups. Data was subjected to a standard analysis of covariance where tumor size was regressed on time with treatment as a covariate. The results showed that reduction in tumor size over time for the DC101 group was significantly different ($p<0.0001$) from that seen for 2A13 injected mice.

Figure 17:
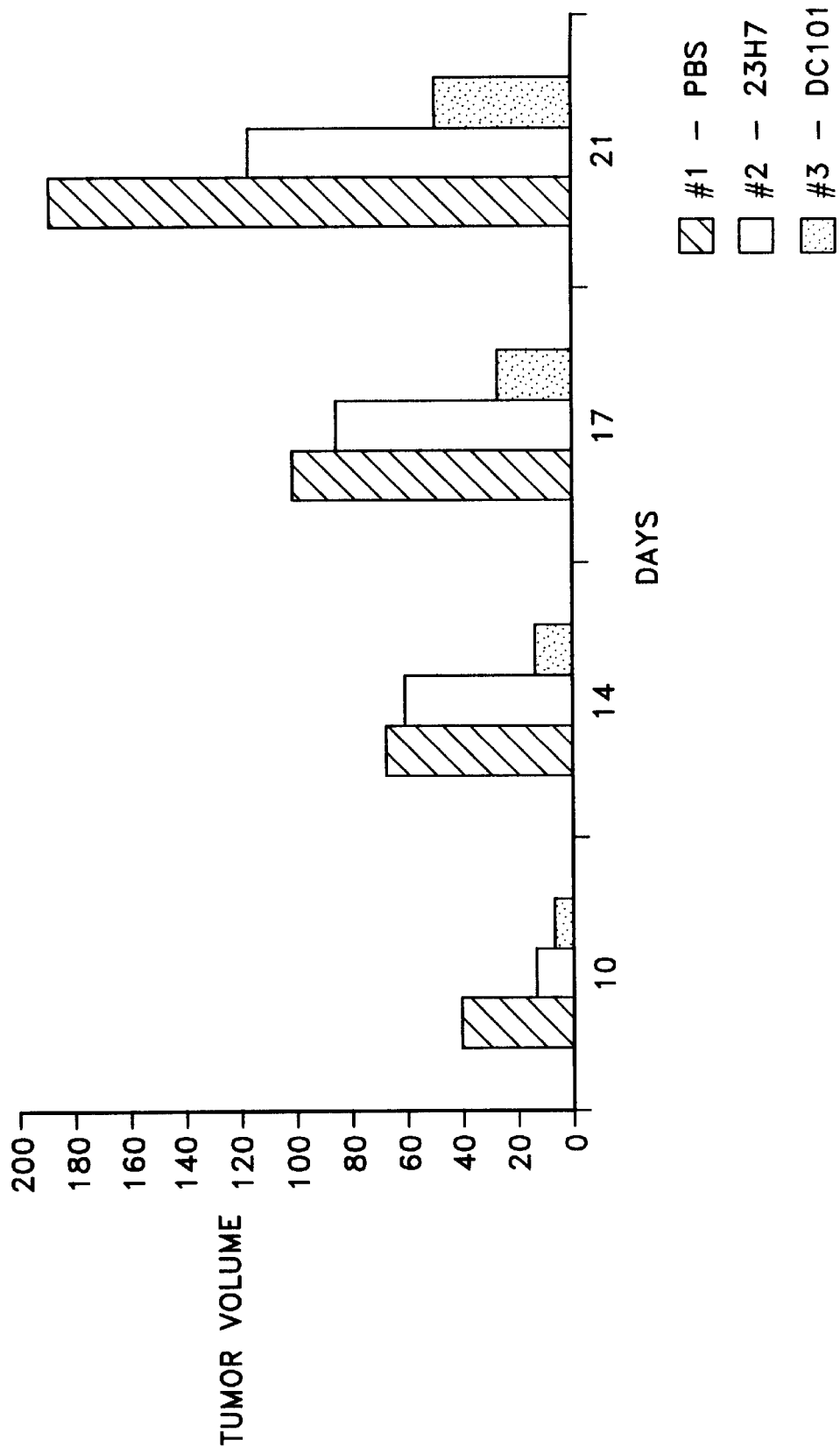
FIG. 17: Athymic nude mice were injected subcutaneously with human glioblastoma cell line GBM-18 and divided into three groups: a PBS control, an irrelevant rat lgG1 control 23H7, and DC101. Treatments were administered simultaneously with tumor xenografts and continued for four weeks.

FIG. 17 shows the therapeutic efficacy of DC101 in athymic nude mice transplanted with the human glioblastoma tumor cell line GBM-18, which secretes VEGF. Nude mice were injected subcutaneously with GBM-18 cells and divided into three groups of treatment: a PBS control, an irrelevant rat IgG1 control, and DC101. Treatments were administered simultaneously with tumor xenografts and continued for four weeks. The results showed that GBM-18 tumor growth in DC101 treated nude mice was significantly reduced relative to controls. This experiment indicates that DC101 suppresses tumor growth by blocking VEGF activation of FLK-1 on tumor associated vascular endothelial cells, and that DC101 has therapeutic value as an anti-angiogenic reagent against vascularized tumors secreting VEGF.

Monoclonal antibodies to FLK-1 receptor tyrosine kinase inhibit tumor invasion by abrogating angiogenesis. Invasive growth and angiogenesis are essential characteristics of malignant tumors. Both phenomena proved to be suitable to discriminate benign from malignant keratinocytes in a surface transplantation assay. After transplantation of a cell monolayer attached to a collagen gel onto the back muscle of nude mice, all tumor cells initially formed organized squamous epithelia, but only malignant keratinocytes grew invasively within 2–3 weeks. Both benign and malignant cells induced angiogenesis. Angiogenic response to malignant cells, however, occurred earlier, is much stronger, and capillary growth directed toward malignant epithelia. Moreover, in transplants of benign tumor cells, capillaries regressed after 2–3 weeks, whereas malignant keratinocytes maintain the level of ongoing angiogenesis. The vascular endothelial growth factor (VEGF) and its cognate receptor play a pivotal role in tumor angiogenesis. The administration of DC101 disrupted ongoing angiogenesis leading to inhibition of tumor invasion. The antibody prevented maturation and further expansion of newly formed vascular network, but did not significantly interfere with initial angiogenesis induction. These results provide evidence that tumor invasion requires precedent angiogenesis, and that the VEGF receptors are crucial in maintaining angiogenesis in this model system.

Figure 15:
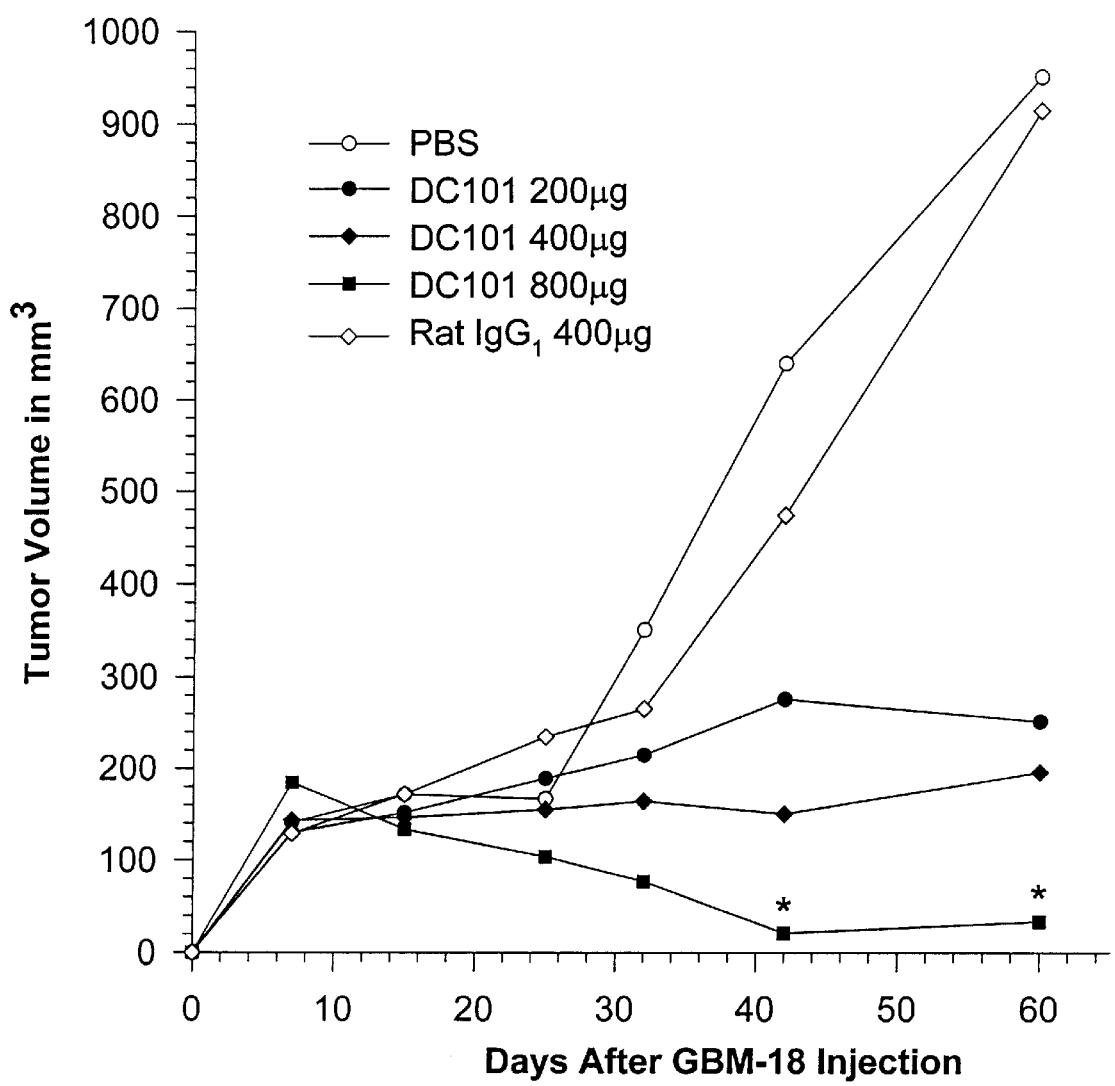
FIG. 15: Effect of different concentrations of DC101 treatments on established glioblastona (gbm-18) tumors.

Example VII-2. Effect of different concentrations of DC101 on established glioblastoma (gbm-18) tumors Athymic mice (nu/nu) were inoculated subcutaneously with GBM-18 (human glioblastoma multiformae). The results are shown in FIG. 15. Antibody therapy was initiated when the tumors reached an average volume of 100–200 mm$^3$. Treatment consisted of six injections (twice weekly for 3 weeks) of the following: (i) DC-101 at 200, 400 or 800 ug/injection; (ii) an irrelevant isotype matched rat IgG (400 ug/injection); or, (iii) PBS. Tumor volumes were measured with a caliper. Tumor inhibition in the DC-101 groups was found to be significant (*) vs. the PBS and irrelevant monoclonal antibody groups.

Figure 12:
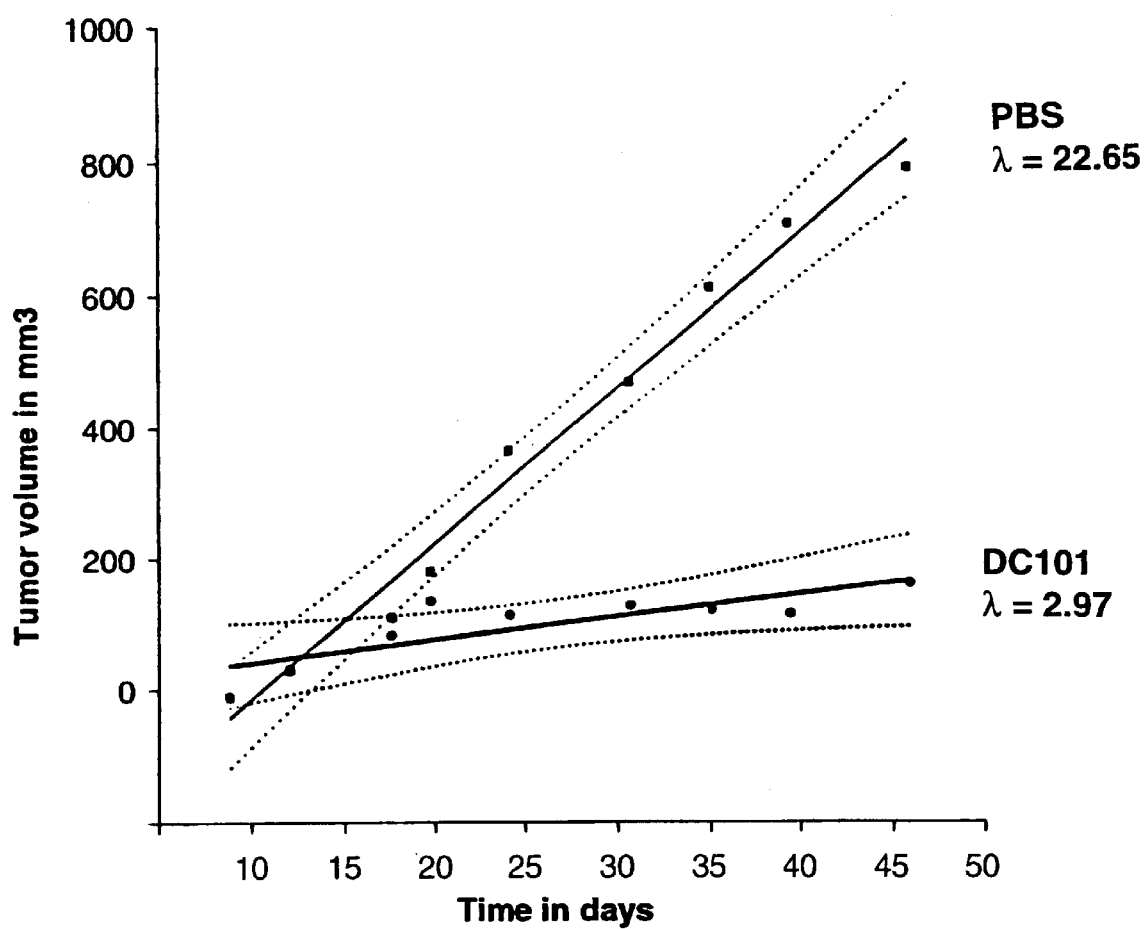
FIG. 12: Effects of rat anti-FLK-1 monoclonal antibody DC101 on the growth of GBM-18 tumors is nude mice.

FIG. 12 shows the results of another experiment deemonstrating the effects of the rat anti-FLK-1 monoclonal antibody DC101 on the growth of GBM-18 tumors in nude mice. Animals (nu/nu; Charles River Labs; ten animals per group) were injected subcutaneously with GBM-18 cells (human glioblastoma [100]; 1 million per animal) on day 0. Treatments with PBS or DC101 (200 μg per injection) were begun on day 7 and continued twice weekly for 3 weeks (6×). Graphs show a plot of the mean tumor volumes and regressed data for each group over time with their respective tumor growth rates (slopes given as λ; solid lines) and 99% confidence limits (dotted lines). The slope of the line for animals treated with DC101 was significantly different from that of PBS ($p \leq 0.01$). It is important to note that an irrelevant rat IgG1 monoclonal antibody (anti-mouse IgA; Pharmigen) had no effect on the growth of GBM-18 xenografts and gave results similar to that observed with PBS (data not shown).

SUPPLEMENTAL ENABLEMENT

The invention as claimed is enabled in accordance with the above specification and readily available references and starting materials. Nevertheless, Applicants have deposited with the American Type Culture Collection, 12301 Parklawn Drive, Rockville, Md., 20852 USA (ATCC) the hybridoma cell lines that produce the monoclonal antibodies listed below:

Hybridoma cell line DC101 producing rat anti-mouse FLK-1 monoclonal antibody deposited on Jan. 26, 1994 (ATCC Accession Number HB 11534).

Hybridoma cell line M25.18A1 producing mouse anti-mouse FLK-1 monoclonal antibody Mab 25 deposited on Jul. 19, 1996 (ATCC Accession Number HB 12152).

Hybridoma cell line M73.24 producing mouse anti-mouse FLK-1 monoclonal antibody Mab 73 deposited on Jul. 19,1996 (ATCC Accession Number HB 12153).

These deposits were made under the provisions of the Budapest Treaty on the International Recognition of the Deposit of Microorganisms for the Purposes of Patent Procedure and the regulations thereunder (Budapest Treaty). This assures maintenance of a viable culture for 30 years from date of deposit. The organism will be made available by ATCC under the terms of the Budapest Treaty, and subject to an agreement between Applicants and ATCC which assures unrestricted availability upon issuance of the pertinent U.S. patent. Availability of the deposited strains is not to be construed as a license to practice the invention in contravention of the rights granted under the authority of any government in accordance with its patent laws.

What is claimed is:

1. Isolated nucleic acid molecules comprising a nucleic acid sequence that encodes an amino acid sequence wherein the amino acid sequence consists of the variable region of a monoclonal antibody that specifically binds to an extracellular domain of a VEGF receptor and neutralizes activation of the receptor.

2. The nucleic acid of claim 1, wherein the monoclonal antibody is produced by hybridoma cell line DC101 deposited as ATCC Accession No, HB 11534.

3. The nucleic acid of claim 1, wherein the monoclonal antibody is produced by hybridoma cell line M25.18Al deposited as ATCC Accession No. HB 12152.

4. The nucleic acid of claim 1, wherein the monoclonal antibody is produced by hybridoma cell line M73.24 deposited as ATCC Accession No. HB 12153.

5. Isolated nucleic acid molecules comprising a nucleic acid sequence that encodes an amino acid sequence wherein the amino acid sequence consists of the hypervariable region of a monoclonal antibody that specifically binds to an extracellular domain of a VEGF receptor and neutralizes activation of the receptor.

6. The nucleic acid of claim 5, wherein the monoclonal antibody is produced by hybridoma cell line DC101 deposited as ATCC Accession No. HB 11534.

7. The nucleic acid of claim 5, wherein the monoclonal antibody is produced by hybridoma cell line M25.18A1 deposited as ATCC Accession No. HB 12152.

8. The nucleic acid of claim 5, wherein the monoclonal antibody is produced by hybridoma cell line M73.24 deposited as ATCC Accession No. HB 12153.

* * * * *

UNITED STATES PATENT AND TRADEMARK OFFICE
CERTIFICATE OF CORRECTION

PATENT NO. : 5,861,499
DATED : January 19, 1999
INVENTOR(S) : Rockwell, et al.

It is certified that error appears in the above-indentified patent and that said Letters Patent is hereby corrected as shown below:

IN THE TITLE:

On Page 1, and column 1, lines 4-5.
now reads "Extracellular Domain",
should read --Extracellular Domain of a VEGF Receptor--.

IN THE SPECIFICATION:

In Column 1, line 5,
now reads "Extracellular Domain",
should read --Extracellular Domain of a VEGF Receptor--.

In Column 1, line 6-8,
now reads "This application is a continuation-in-part of Serial No. 08/476,533",
should read --This application is a continued prosecution application of Serial No. 08/706,804 filed on September 3, 1996, withdrawn from issue and abandoned; which is a continuation-in-part of Serial No. 08/476,533--.

In Column 1, line 8,
now reads "Jun. 27, 1995, now abandoned;",
should read --Jun. 7, 1995, now abandoned--.

In Column 1, line 64,
now reads "class IIII",
should read --class III--.

In Column 3, line 25,
now reads "at stimulatory concentrtions",
should read --at maximal stimulatory concentrations--.

UNITED STATES PATENT AND TRADEMARK OFFICE
CERTIFICATE OF CORRECTION

PATENT NO. : 5,861,499
DATED : January 19, 1999
INVENTOR(S) : Rockwell, et al.

It is certified that error appears in the above-indentified patent and that said Letters Patent is hereby corrected as shown below:

In Column 4, line 27,     now reads "phophotyrosine", should read --phosphotyrosine--.

In Column 5, line 8,     now reads "glioblastona", should read --glioblastoma--.

In Column 7, line 16,     now reads "charaqcterized", should read --characterized--.

In Column 9, line 4,     now reads "NatI.", should read --Natl.--.

In Column 9, line 49,     now reads "NatI.", should read --Natl.--.

In Column 11, line 58,     now reads "PL;", should read --$P_L$;--.

In Column 12, line 13,     now reads "NatI.", should read --Natl.--.

In Column 13, line 53-54,     now reads "produciton", should read --production--.

In Column 13, line 57,     now reads "witha", should read --with a --.

UNITED STATES PATENT AND TRADEMARK OFFICE
CERTIFICATE OF CORRECTION

PATENT NO. : 5,861,499
DATED : January 19, 1999
INVENTOR(S) : Rockwell, et al.

Page 3 of 5

It is certified that error appears in the above-indentified patent and that said Letters Patent is hereby corrected as shown below:

In Column 13, line 62,  now reads "FLK-I/SEAP", should read --FLK-1/SEAP--.

In Column 14, line 58,  now reads "Tris-HCI", should read --Tris-HC1--.

In Column 15, line 2,  now reads "NatI.", should read --Natl.--.

In Column 17, line 33,  now reads "WITH", should read --WITH DC101--.

In Column 17, line 53,  now reads "$VEGF_{,165}$", should read --$VEGF_{165}$--.

In Column 17, line 57,  now reads "ug/mi", should read --ug/ml--.

In Column 17, line 61,  now reads "Underthese", should read --Under these--.

In Column 2, line 63,  now reads "1gG1k", should read --IgG1k--.

UNITED STATES PATENT AND TRADEMARK OFFICE
CERTIFICATE OF CORRECTION

PATENT NO. : 5,861,499
DATED : January 19, 1999
INVENTOR(S) : Rockwell, et al.

It is certified that error appears in the above-indentified patent and that said Letters Patent is hereby corrected as shown below:

In Column 4, line 15,  now reads "anti-FLK2 1gG2a",
should read --anti-FLK2 IgG1--.

In Column 4, line 15,  now reads "rat anti-FLK-1 1gG2a",
should read --rat anti-FLK1 IgG2a--.

In Column 5, line 17,  now reads "irrelevant rat 1gG1",
should read --irrelevant rat IgG1--.

In Column 19, line 31,  now reads "5 ug/mI",
should read --5 ug/ml--.

In Column 21, line 56,  now reads "dc101",
should read --DC101--.

UNITED STATES PATENT AND TRADEMARK OFFICE
CERTIFICATE OF CORRECTION

PATENT NO. : 5,861,499
DATED : January 19, 1999
INVENTOR(S) : Rockwell, et al.

It is certified that error appears in the above-identified patent and that said Letters Patent is hereby corrected as shown below:

In Column 22, line 16,   now reads "16B shows",
                         should read --16B show--.

In Column 23, line 21,   now reads "deemonstrating",
                         should read --demonstrating--.

In Column 24, line 28,   now reads "No,",
                         should read --No.--.

Signed and Sealed this

Fourth Day of July, 2000

Attest:

Q. TODD DICKINSON

*Attesting Officer*        *Director of Patents and Trademarks*